(12) United States Patent
Kweon et al.

(10) Patent No.: US 10,682,333 B2
(45) Date of Patent: Jun. 16, 2020

(54) COMPOSITION FOR INHIBITING FORMATION OF SNARE COMPLEX, CONTAINING MYRICETIN DERIVATIVES

(71) Applicant: RESEARCH & BUSINESS FOUNDATION SUNGKYUNKWAN UNIVERSITY, Suwon-si (KR)

(72) Inventors: Dae Hyuk Kweon, Suwon-si (KR); Joon Bum Park, Seoul (KR); Young Hun Jung, Seoul (KR); Woo Jae Chung, Suwon-si (KR); Pa Ul Heo, Seoul (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 0 days.

(21) Appl. No.: 15/748,500

(22) PCT Filed: Jul. 29, 2016

(86) PCT No.: PCT/KR2016/008333
§ 371 (c)(1),
(2) Date: Apr. 16, 2018

(87) PCT Pub. No.: WO2017/018847
PCT Pub. Date: Feb. 2, 2017

(65) Prior Publication Data
US 2018/0222878 A1    Aug. 9, 2018

(30) Foreign Application Priority Data

Jul. 30, 2015  (KR) .................. 10-2015-0108322
Jul. 15, 2016  (KR) .................. 10-2016-0090116

(51) Int. Cl.
*A61K 31/352*   (2006.01)
*A61Q 19/00*    (2006.01)
(Continued)

(52) U.S. Cl.
CPC ............ *A61K 31/352* (2013.01); *A61K 8/498* (2013.01); *A61Q 19/00* (2013.01); *A61Q 19/08* (2013.01); *C07D 311/30* (2013.01)

(58) Field of Classification Search
CPC ........................... A61K 31/352; C07D 311/30
See application file for complete search history.

(56) References Cited

U.S. PATENT DOCUMENTS 8,263,643 B2 *  9/2012  Kweon .................. A61K 31/35
                                             514/453

FOREIGN PATENT DOCUMENTS

CN       102875620 A    1/2013
KR       20080083438 A  9/2008
(Continued)

OTHER PUBLICATIONS

Funayama et al. (Natural Medicines 49(3), 322-328 (1995)).*
(Continued)

*Primary Examiner* — Valerie Rodriguez-Garcia
(74) *Attorney, Agent, or Firm* — NSIP Law

(57) ABSTRACT

The present invention relates to a composition for inhibiting the formation of a SNARE complex, containing myricetin derivatives, and having novel structures and obtained by the acylation of myricetin, laricitrin, combretol, or syringetin. The myricetin derivatives are considered to exhibit an effect of being bioconverted into myricetin in a cell. The myricetin derivatives lost the dark color of conventional myricetin and properties thereof were changed such that the myricetin derivatives have properties of photostability and fat solubility. Therefore, since stable form myricetin derivatives are absorbed into a cell such that an activity, possessed by normal myricetin, of inhibiting the formation of a SNARE complex are exhibited, the present invention can exhibit an excellent function as a SNARE targeting prodrug, and as a
(Continued)

composition for inhibiting the formation of a SNARE complex, containing the same.

4 Claims, 12 Drawing Sheets

(51) Int. Cl.
    *A61K 8/49*       (2006.01)
    *A61Q 19/08*     (2006.01)
    *C07D 311/30*   (2006.01)

(56) References Cited

FOREIGN PATENT DOCUMENTS

| KR | 10-2011-0017599 | * | 2/2011 |
| WO | 2014012075 A2 | | 1/2014 |
| WO | WO 2014/012075 | * | 1/2014 |

OTHER PUBLICATIONS

Mainini (J. Am. Oil. Chem. Soc. (2013) 90:1751-1759).*
Venditti et al. (Fitoterapia 95 (2014) 182-185).*
Clarins document—year 2011.*
Mani et al. (Journal of the Tennessee of Science 68 (3):83-86 (1993)).*
Duthie et al. (Mutation Research 393 (1997) 223-231).*
Mastuda et al. (Bioorg. Med. Chem. 10 (2002) p. 3123-3128).*
Mainini et al., "Synthesis, Molecular Characterization and Preliminary Antioxidant Activity Evaluation of Quercetin Fatty Esters", J Am Oil Chem Soc, 2013, vol. 90, No. 11, pp. 1751-1759.
Kaihatsu et al., "Potential Anti-Influenza Virus Agents Based on Coffee Ingredients and Natural Flavonols", Nat Prod Chem Res, 2014, vol. 2, No. 2, pp. 1-7.
Cho et al, "Characterization of Regiospecific Flavonoid 3'/5'-O-Methyltransferase from Tomato and its Application in Flavonoid Biotransformation", J Korean Soc Appl Biol Chem, 2012, vol. 55, No. 6, pp. 749-755.
Kawano et al., "The Partial Demethylation of Flavones. III, Preparation of Rhamnetin and 7-O-Methylmyricetinn", Chem. Pharm, Brill., 1967, vol. 15, No. 5, pp. 711-712.
Demetzos et al., "Structure Elucidation, Conformational Analysis and Thermal Effects on Membrane Bilayers of an Antimicrobial Myricetin Ether Derivative", J. Heterocyclic Chem., 2001, vol. 38, No. 3, pp. 703-710.
Woska et al., "SNARE complex-mediated degranulation in mast cells", J. Cell. Mol. Med., 2012, vol. 16, No. 4, pp. 649-656.
Weber et al., "SNAREpins: Minimal Machinery for Membrane Fusion", CELL, 1998, vol. 92, pp. 759-772.
International Search Report for International Application No. PCT/KR2016/008333 (3 Pages) ( dated Nov. 1, 2016).

* cited by examiner

D : DMSO   MA : Hexa-O-acetylmyricetin
M : Myricetin   Z : Zinc oxide

COMPOSITION FOR INHIBITING FORMATION OF SNARE COMPLEX, CONTAINING MYRICETIN DERIVATIVES

STATEMENT REGARDING GOVERNMENT SPONSORED RESEARCH

The present invention was undertaken with the support of 1) Development of neuromoulatory SNARE-wedging materials No. 1465017087 grant funded by the Korea Health Industry Development Institute, 2) Center for Human Interface Nano Technology No. 1711010677 grant funded by the National Research Foundation of Korea.

CROSS-REFERENCE TO RELATED APPLICATIONS

This application is a 371 of PCT/KR2016/008333, filed Jul. 29, 2016, which claims the benefit of priority from Korean Patent Application No. 10-2016-0090116, filed Jul. 15, 2016 and Korean Patent Application No. 10-2015-0108322, filed Jul. 30, 2015, the contents of each of which are incorporated herein by reference.

TECHNICAL FIELD

The present invention relates to a composition for inhibiting the formation of a soluble N-ethylmaleimide-sensitive factor attachment protein receptor (SNARE) complex, which includes a myricetin derivative.

BACKGROUND ART

SNARE (soluble N-ethylmaleimide-sensitive factor attachment protein receptor; SNAP receptor) proteins are a large protein superfamily consisting of 60 or more members in yeasts and mammalian cells, and the primary role of SNARE proteins is to mediate vesicle fusion. That is, SNARE proteins mediate the fusion of vesicles with their target membrane bound to compartments such as a lysosome. As a specific example, SNAREs mediate docking of synaptic vesicles with the presynaptic membrane in neurons.

Meanwhile, to regulate the relaxation and contraction of muscles, there is a neuromuscular junction in the upper layer of muscle, and synaptic vesicles are loaded in this nerve terminal. Muscles contract by receiving a message of a neurotransmitter transmitted from the inside of synaptic vesicles, and for the release of such a neurotransmitter, SNARE proteins form a complex, and this enables neurotransmitters to be docking with muscles. In particular, for the release of a neurotransmitter, a synaptic vesicle containing the neurotransmitter is required to be fused with a presynaptic membrane so that a passage between two boundaries can be formed, and at this time, a fundamental force for such membrane fusion is provided by SNARE complexes comprising three kinds of proteins. Particularly, a release passage of a neurotransmitter is opened by membrane fusion between a synaptic vesicle and a presynaptic membrane, and a t-SNARE complex, which is a complex of a syntaxin-1a protein and a SNAP-25 protein that are attached to a target membrane, and v-SNARE attached to a vesicle are involved in this pathway, and such SNARE proteins are twisted in a spiral shape.

In the membrane fusion, the rearrangement of a lipid bilayer, which is widely known in the art, occurs. Since biomembranes strongly repel against each other, the membranes cannot be spontaneously fused, and thus a strong external force is required to overcome the repulsive force between the membranes. At this time, SNARE proteins generate such a strong force enough to overcome the repulsive force between the membranes. That is, the formation of a SNARE complex is a source of the force to overcome intermembrane repulsive force and is a main action in extracellular exocytosis including the release of a neurotransmitter [Weber etc., Cell, 92, 759-772 (1998)].

As an example, pores of the skin are generally distributed in the facial skin but can be visually recognized particularly in nasal and buccal sites, and the appearance of pores varies from person to person according to intrinsic and extrinsic factors such as gender, genetic factors, aging, acnes, chronic UV exposure, and the like. The reason for the widening of the pores is that as sebum is excessively secreted or skin aging begins, collagen fibers and elastic fibers, which support pore walls, are denatured and decreased, resulting in loss of skin elasticity and skin laxity. Since the contraction or relaxation of muscles (arrector pili muscles) attached to hairs is under the control of the sympathetic and parasympathetic nerves, the pores may be reduced or enlarged by neural control. The sympathetic nerve is slightly distant from muscles and narrows pores, whereas the parasympathetic nerve is located near muscles and enlarges pores. When the parasympathetic nerve is selectively suppressed, a compensating action of the sympathetic nerve contracts muscles attached to hairs, thereby reducing pores.

On the other hand, if the conjugation and twisting of SNARE are not fully completed, membrane fusion fails, and, accordingly, the release of neurotransmitters does not occur, and this eventually results in no movement of muscles. This indicates that, through this process, the generation of wrinkles produced by frequently used muscles can be prevented and pre-formed wrinkles can also be alleviated. In addition, by inhibiting the release of neurotransmitters, hyperhidrosis, which refers to excessive sweating caused by the stimulation of sweat glands due to the release of a larger amount of neurotransmitters than required, may be alleviated.

In other words, due to the SNARE formation inhibitory effect, the generation of wrinkles caused by the movement of muscles may be inhibited and the formed wrinkles may be alleviated, and hyperhidrosis, which is one of the diseases caused by excessive release of neurotransmitters, may be treated, prevented, and alleviated.

Furthermore, in a case in which the formation of SNARE protein complexes specific to mast cells in vivo is inhibited, mast cell degranulation is inhibited, and allergic diseases and autoimmune diseases are thereby treated and prevented (Woska J. R. Jr. and Gillespie M. E., J. Cell Mol. Med., 2012, 16(4), 649-656).

Representative materials targeting the SNARE include bacterial neurotoxin which causes botulism food poisoning and tetanus, and the like. For example, a neurotoxin derived from *Clostridium botulinum* is a main ingredient of a drug known as "Botox," which is known to be used mainly in cosmetic procedures such as wrinkle removal, or the like, and is used also to treat the secretion of many neurotransmitters and/or muscle-related diseases, such as strabismus, blepharospasm, vocal cord dysfunction, torticollis, cardiomyopathy, ulcer and gastric acid reflux disorders, appetite decrease, pancreatic diseases, stretchmarks, overactive bladder, anal fissure, poliomyelitis, muscular pain, hip deformities, hyperhidrosis, back pain, neck pain, chronic headache, cranial nerve disorder, and the like. Specifically, Botox is known to exhibit a therapeutic effect on the above-listed diseases because a neurotoxin, which is a main ingredient of Botox, inhibits complex formation by acting specifically on SNARE present in neurons, thus suppressing membrane fusion, resulting in blocking of the release of neurotransmitters, thereby inhibiting the movement of muscles or the sympathetic or parasympathetic nervous system. However, Botox components are toxic substances and thus may cause side effects; therefore, there is a need to be cautious in determining a dose or application site thereof.

DISCLOSURE

Technical Problem

As a result of having made intensive efforts to develop a drug having an effect of inhibiting the formation of SNARE complexes and thus exhibiting a pharmacological activity similar to that of Botox and having decreased cytotoxicity and increased stability, the inventors of the present invention verified that myricetin derivatives, in which one or more hydroxyl groups of myricetin are alkylated or acylated, exhibited an effect of inhibiting the formation of SNARE complexes and was not discolored and/or colored even when exposed to UV due to significantly improved stability, and, accordingly, could be effectively used in a cosmetic composition, and the like, and thus completed the present invention.

Technical Solution

An object of the present invention is to provide a substance suitable for use as a prodrug targeting soluble N-ethylmaleimide-sensitive factor attachment protein receptor (SNARE) that has no issue related to color, reactivity, strong oxidizing action against sunlight, and the like, and a composition for inhibiting the formation of a SNARE complex, which includes the substance. The present invention also provides a substance suitable for use as a SNARE-targeting prodrug having a more improved activity of inhibiting the formation of SNARE complexes than that of conventional myricetin, and a composition for inhibiting the formation of a SNARE complex, which includes the substance.

Furthermore, the present invention provides a pharmaceutical composition for the prevention or treatment of skin wrinkles, pain, hyperhidrosis, pore enlargement, or allergy, which includes the above-described composition, and a cosmetic composition for alleviating skin wrinkles, allergic symptoms, or pores.

Advantageous Effects

The present invention is effective in that novel myricetin derivatives obtained by acylating myricetin, as well as laricitrin, combretol, and syringetin, which are myricetin derivatives, have an activity of inhibiting the formation of SNARE complexes in vivo, but do not have an activity of inhibiting the formation of SNARE complexes in vitro, and thus can be applied as a SNARE-targeting prodrug.

BEST MODE

An embodiment of the present invention provides a composition for inhibiting the formation of a soluble NSF attachment protein receptor (SNARE) complex, which includes a compound represented by Formula 1 below or a pharmaceutically acceptable salt thereof as an active ingredient.

[Formula 1]

wherein, in Formula 1 above, each of $R_1$, $R_2$, $R_3$, $R_4$, $R_5$, and $R_6$ is independently hydrogen, linear or branched $C_{1-4}$ alkyl, or linear or branched, saturated or unsaturated $C_{1-20}$ acyl, the alkyls or the acyls may be identical to or different from each other, and not all of $R_1$, $R_2$, $R_3$, $R_4$, $R_5$, and $R_6$ are hydrogen.

Hereinafter, the present invention will be described in detail.

Figure 1:
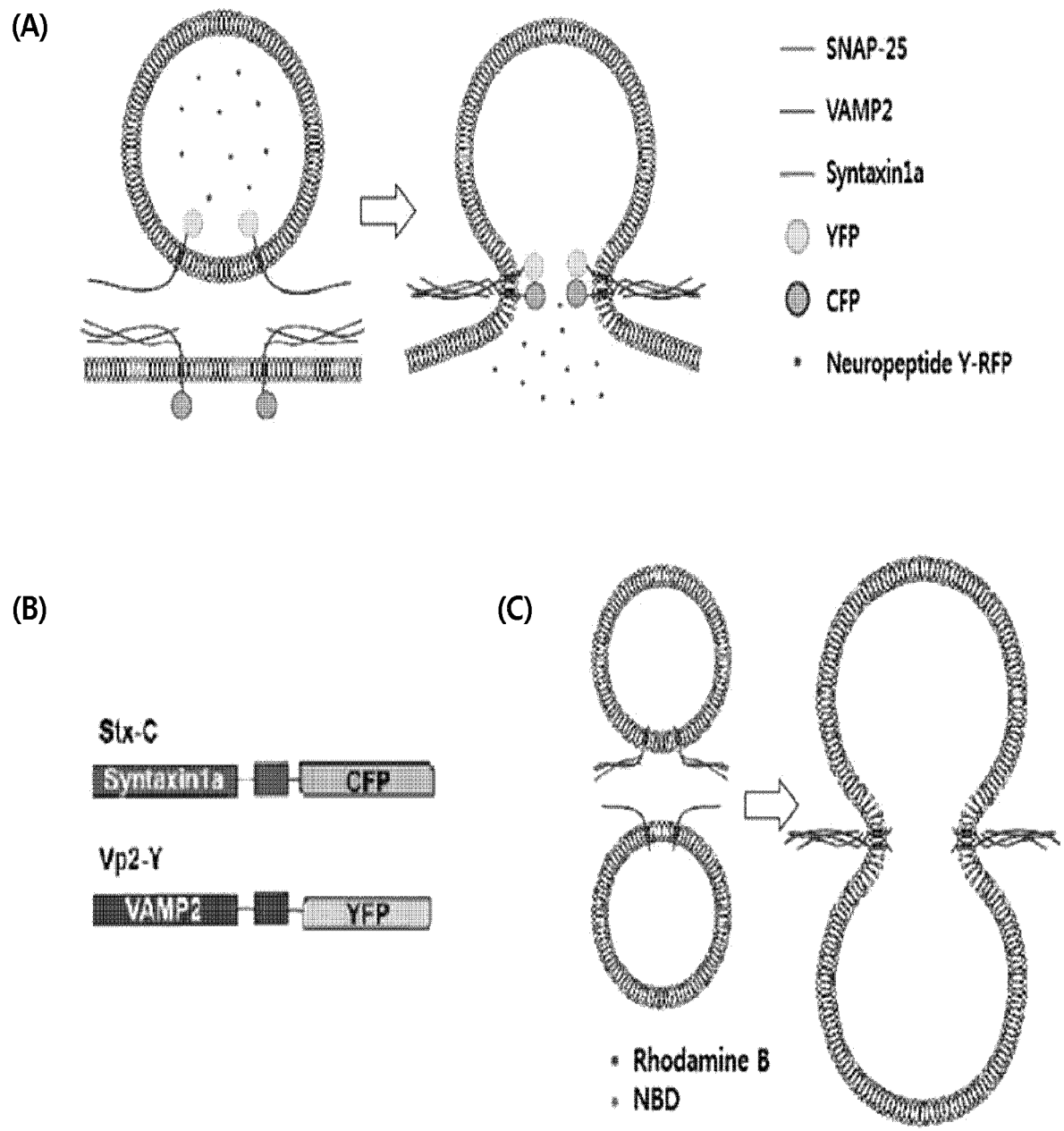
FIG. 1 schematically illustrates a screening system for verifying an effect of a prodrug according to the present invention.

In the present invention, various candidate materials were screened to develop a prodrug having an activity similar to that of commercially widely known Botox, and previous studies have confirmed that, among these candidate materials, derivatives of polyphenols (myricetin, delphinidin, and cyanidin), which are known to act as a SNARE inhibitor, are possibly used as the prodrug. In particular, myricetin is known to interrupt the formation of a SNARE complex through insertion of myricetin thereinto to stop SNARE-mediated membrane fusion, leaving the complex in a hemifusion state. However, there are some issues to address before replacing Botox, which is used mainly for cosmetic purposes, with myricetin. The issues are related mostly to chemical structures, such as the issues of color, reactivity, and the like. In the present invention, while an alternative to overcoming these problems had been sought through a screening method (see Example 1) of FIG. 1, it has been found that the compound represented by Formula 1, which is a myricetin derivative, has the ability to inhibit the formation of a SNARE complex in vivo and thus can be used as a SNARE-targeting prodrug. The present invention is based on this finding.

In particular, in one embodiment of the present invention, it was confirmed that laricitrin, combretol, and syringetin, which are methylated forms of myricetin, had the ability to inhibit the formation of a SNARE complex in vivo, and thus could be used as a SNARE-targeting prodrug (see Example 2).

Laricitrin, combretol, and syringetin, which are natural derivatives of myricetin, may be represented by Formulae 2, 3, and 4, respectively.

[Formula 2]

[Formula 3]

[Formula 4]

In addition, in one embodiment of the present invention, a novel myricetin derivative corresponding to the compound represented by Formula 1 was prepared by acylation of myricetin using an acyl donor in the presence of a lipase catalyst, and it was confirmed that the prepared myricetin derivative had the ability to inhibit the formation of a SNARE complex in vivo and thus could be used as a SNARE-targeting prodrug (see Example 3).

In addition, in one embodiment of the present invention, a myricetin derivative in which all $R_1$, $R_2$, $R_3$, $R_4$, $R_5$, and $R_6$ are acylated by a fatty acid-derived acyl group was prepared as a novel myricetin derivative corresponding to the compound of Formula 1 by acylating myricetin by reacting the same with a fatty acid as an acyl donor and oxalyl chloride in the presence of a base, and it was confirmed that the prepared myricetin derivative had the ability to inhibit the formation of a SNARE complex in vivo and thus could be used as a SNARE-targeting prodrug (see Example 4).

The composition for inhibiting the formation of a SNARE complex according to the present invention may include a compound represented by Formula 1 below as an active ingredient.

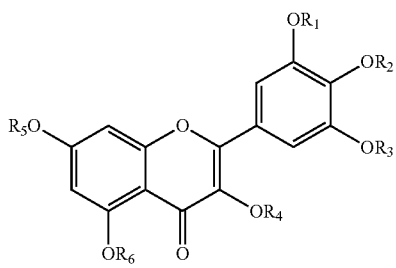

[Formula 1]

wherein, in Formula 1 above, each of $R_1$, $R_2$, $R_3$, $R_4$, $R_5$, and $R_6$ is independently hydrogen, linear or branched $C_{1-4}$ alkyl, or linear or branched, saturated or unsaturated $C_{1-20}$ acyl, the alkyls or the acyls may be identical to or different from each other, and not all of $R_1$, $R_2$, $R_3$, $R_4$, $R_5$, and $R_6$ are hydrogen.

Preferably, the compound represented by Formula 1 may be selected from compounds represented by Formulae 1a to 1d:

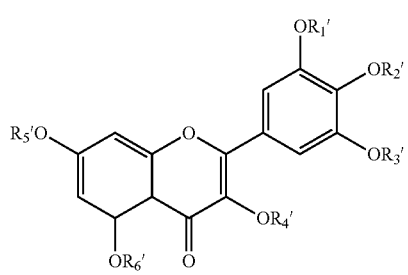

[Formula 1d]

wherein, in Formulae 1a to 1d above, each of $R_1'$, $R_2'$, $R_3'$, $R_4'$, $R_5'$, and $R_6'$ is independently linear or branched, saturated or unsaturated $C_{1-20}$ acyl, and the acyls may be identical to or different from each other.

The acyl group may be selected from the group consisting of an acetyl group, a butyryl group, an octanoyl group, a lauroyl group, a palmitoyl group, a stearoyl group, and an eicosanoyl group. Specifically, the compound represented by Formula 1 suitable for use in the composition for inhibiting the formation of a SNARE complex may be selected from the group consisting of the following compounds:

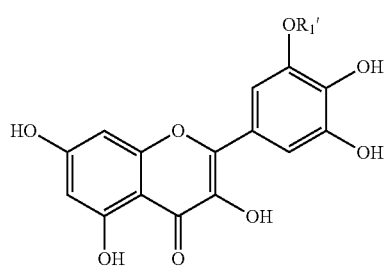

[Formula 1a]

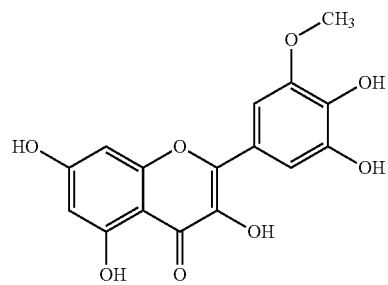

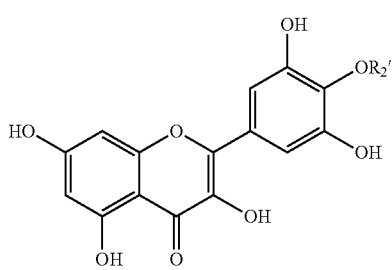

[Formula 1b]

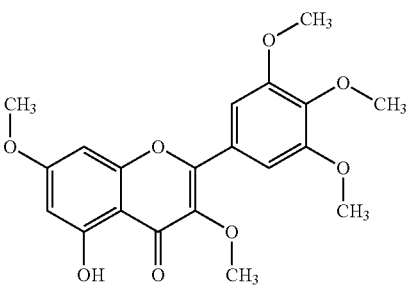

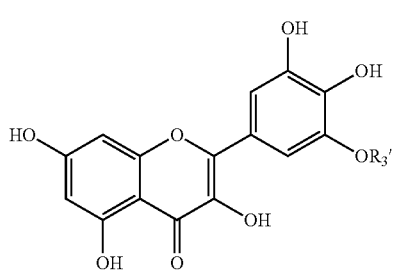

[Formula 1c]

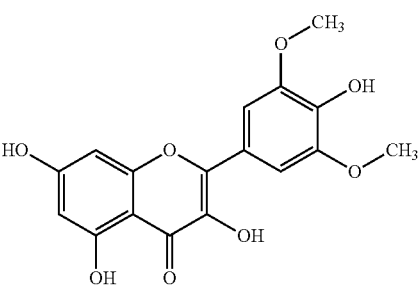

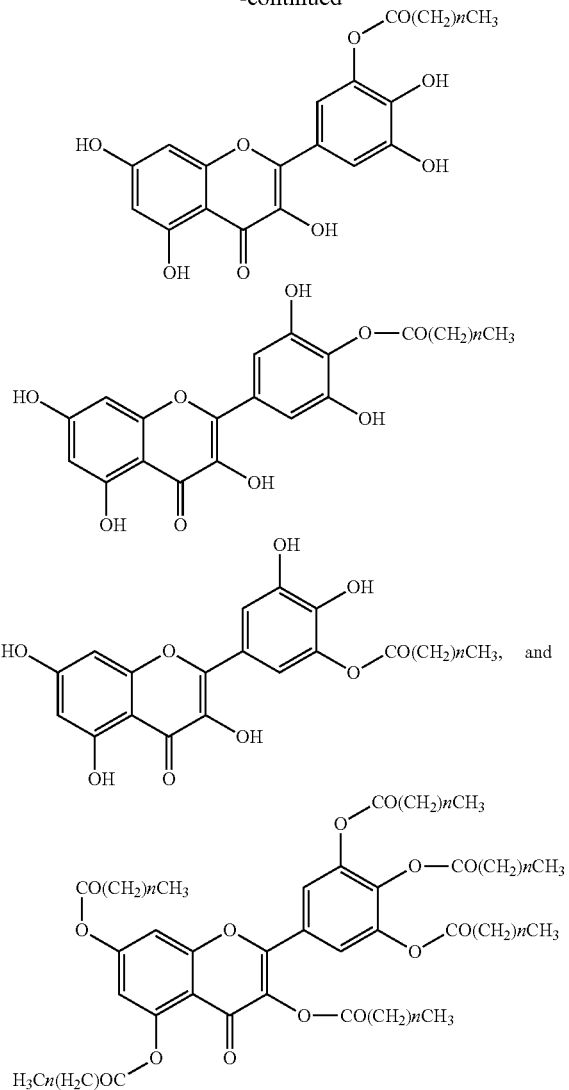

wherein, in the above formulae, n is an integer of 0 to 18.

The composition for inhibiting the formation of a SNARE complex, according to the present invention, may include all of the compound represented by Formula 1a, the compound represented by Formula 1b, and the compound represented by Formula 1c.

In an example embodiment, the composition for inhibiting the formation of a SNARE complex, according to the present invention, may be a pharmaceutical composition or a cosmetic composition.

In the present invention, a disease or symptom that is treated, alleviated, or prevented by inhibiting the formation of a SNARE complex may be skin wrinkles, pain, hyperhidrosis, pore enlargement, an allergic disease, or an autoimmune disease, but the present invention is not limited thereto. The compound of the present invention may effectively inhibit the formation of a SNARE complex like Botox does, and thus may be used in diseases that can be alleviated or treated using Botox without limitation.

For example, the allergic disease may be anaphylaxis, allergic rhinitis, asthma, urticaria, atopic dermatitis, contact dermatitis, or allergic dermatitis, but the present invention is not limited thereto.

Figure 4:
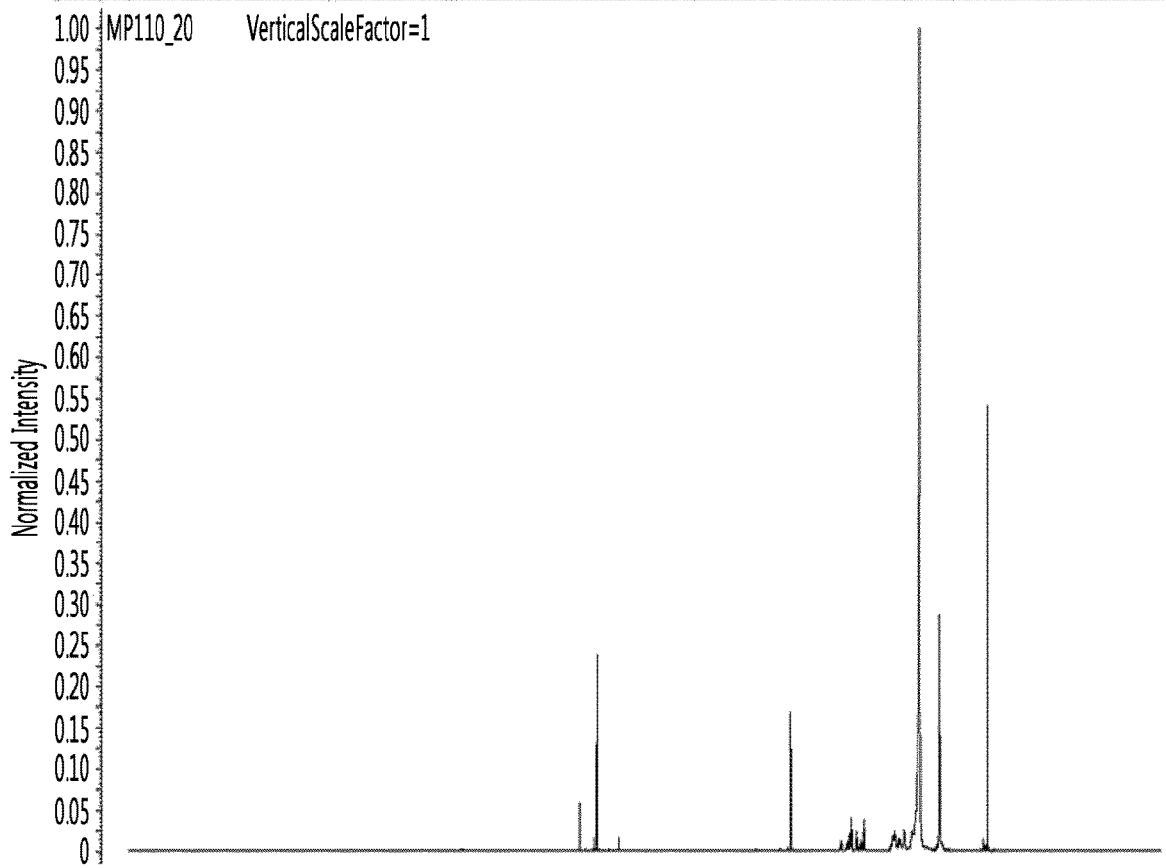
FIG. 4 illustrates $^1$H NMR analysis results of the structure and composition of a mixture containing a myricetin derivative, in which all hydroxyl groups of myricetin were acylated, produced by acylation using palmitic acid as a fatty acid, according to another embodiment of the present invention.

According to one embodiment of the present invention, laricitrin, combretol, and syringetin exhibited an effect of inhibiting the formation of a SNARE complex (see Example 2), and myricetin derivatives were seen to inhibit acetylcholine release in a concentration-dependent manner (see Example 4 and FIG. 4). The myricetin derivatives exhibited an excellent activity of inhibiting acetylcholine release compared to myricetin. The myricetin derivative of the present invention may be effectively used in treating, alleviating, or preventing skin wrinkles, pain, hyperhidrosis, pore enlargement, or an allergic disease by inhibiting the formation of a SNARE complex and suppressing acetylcholine release.

When the composition for inhibiting the formation of a SNARE complex, according to the present invention, is a pharmaceutical composition, the composition may further include a pharmaceutically acceptable carrier.

The term "pharmaceutically acceptable" as used herein refers to describe compositions and molecules that are physiologically acceptable and typically do not cause an unexpected reaction when administered to humans. Preferably, as used herein, the term "pharmaceutically acceptable" is meant to be approved by other generally known pharmacopoeia for use in mammals, in particular humans.

The pharmaceutically acceptable carrier may include various ingredients such as lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate, mineral oil, or the like.

The pharmaceutical composition of the present invention may be administered by nonoral routes, may be administered in the form of a general pharmaceutical preparation, e.g., one of various nonoral preparations for clinical administration, and may be formulated using generally used diluents or excipients such as fillers, extenders, binders, wetting agents, disintegrating agents, surfactants, and the like.

Preparations for nonoral administration include a sterile aqueous solution, a non-aqueous solvent, a suspension, an emulsion, or a freeze-dried preparation. Examples of the non-aqueous solvent and the suspension include propylene glycol, polyethylene glycol, a vegetable oil such as olive oil, an injectable ester such as ethyl oleate, and the like.

A pharmaceutical composition for inhibiting the formation of a SNARE complex, according to the present invention, may exhibit an effect of inhibiting the formation of a SNARE complex when including an effective amount of the compound represented by Formula 1. As used herein, the term "effective amount" refers to the amount of a compound sufficient to exhibit an effect of inhibiting the formation of a SNARE complex. The effective amount of the compound represented by Formula 1 included in the composition of the present invention may vary according to commercialized forms of the composition, application methods of the compound on the skin, residence time of the compound on the skin, or the like. For example, when the composition is to be produced as a drug, the composition may include the compound represented by Formula 1 at a higher concentration than in a case in which the composition is to be produced as a product such as a shampoo, a hair conditioner, a hair pack, or the like that is commonly applied to the skin. Thus, a daily dose of the composition may be determined such that 0.01 mg/kg to 10 mg/kg, preferably 0.1 mg/kg to 1 mg/kg, of the compound represented by Formula 1 is administered, and the composition may be administered once to six times a day. In addition, the dose may be increased or decreased according to age, gender, body weight, the severity of a disease, administration route, or the like. Thus, the dose does not limit the scope of the present invention in any way.

The pharmaceutical composition of the present invention may be used alone or in combination with methods using surgery, radiotherapy, hormone therapy, chemotherapy, and a biological response modifier.

The present invention may also provide an external preparation for the skin for inhibiting the formation of a SNARE complex, which includes the compound represented by Formula 1 as an active ingredient.

When the compound represented by Formula 1 is used as an external preparation for the skin, the external preparation for the skin may further include an adjuvant commonly used in dermatology, such as a fatty substance, an organic solvent, a solubilizer, a thickener, a gelling agent, a softener, an antioxidant, a suspending agent, a stabilizer, a foaming agent, a flavoring agent, a surfactant, water, an ionic or nonionic emulsifier, a filler, a sequestrant, a chelating agent, a preservative, vitamins, a blocking agent, a wetting agent, essential oil, a dye, a pigment, a hydrophilic or hydrophobic activator, lipid vesicles, or other ingredients commonly used in an external preparation for the skin. In addition, the above ingredients may be included in an amount generally used in dermatology.

When the compound represented by Formula 1 is provided in a formulation for external application to the skin, the formulation may be applicable to hair, such as a gel, a cream, a patch, or an aerosol, but the present invention is not limited thereto.

The present invention may also provide a cosmetic composition for inhibiting the formation of a SNARE complex, which includes the compound represented by Formula 1 as an active ingredient.

When the compound represented by Formula 1 is used as a cosmetic, cosmetics prepared by including the compound represented by Formula 1 as an active ingredient may be in general emulsified and solubilized formulation. The examples of such formulation include sprays, hair gels, hair packs, shampoos, hair conditioners, hair lotions, hair essences, patches, and aerosols.

In addition, the cosmetic may further include, in addition to the compound represented by Formula 1, an adjuvant commonly used in cosmetology, such as a fatty substance, an organic solvent, a solubilizer, a thickener, a gelling agent, a softener, an antioxidant, a suspending agent, a stabilizer, a foaming agent, a flavoring agent, a surfactant, water, an ionic or nonionic emulsifier, a filler, a sequestrant, a chelating agent, a preservative, vitamins, a blocking agent, a wetting agent, essential oil, a dye, a pigment, a hydrophilic or hydrophobic activator, lipid vesicles, or other ingredients commonly used in a cosmetic.

Preferably, the composition of the present invention may be prepared in any formulation applicable to scalp, such as a liquid, cream, paste, solid, or the like, and may be prepared as a composition such as a shampoo, a hair conditioner, a hair lotion, a liquid-type hair growth lotion, or the like for inhibiting the formation of a SNARE complex by including additional general additives. In this case, the formulation also includes aerosols.

The amount of the compound represented by Formula 1 in the composition of the present invention may range from 0.001 wt % to 10 wt %, preferably 0.005 wt % to 5 wt %, and most preferably 0.01 wt % to 3 wt %, with respect to a total weight of the entire composition.

When the amount of the compound represented by Formula 1 is less than 0.001 wt %, it may be difficult to anticipate that a SNARE complex formation inhibitory effect will be exhibited, and when the amount of the compound represented by Formula 1 is greater than 10 wt %, it is difficult to prepare the composition into a suitable formulation or secure long-term stability.

Another embodiment of the present invention also provides a compound represented by Formula 1 below, a mixture including the same, or a pharmaceutically acceptable salt of the compound.

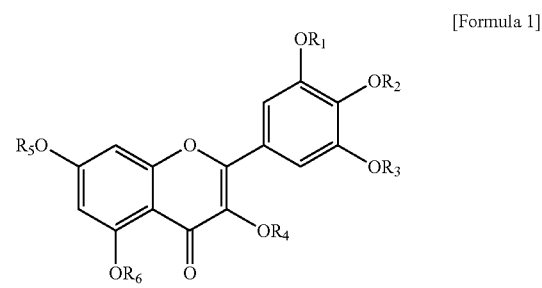

[Formula 1]

wherein, in Formula 1 above, each of $R_1$, $R_2$, $R_3$, $R_4$, $R_5$, and $R_6$ is independently hydrogen, linear or branched $C_{1-4}$ alkyl, or linear or branched, saturated or unsaturated $C_{1-20}$ acyl, the alkyls or the acyls may be identical to or different from each other, and not all of $R_1$, $R_2$, $R_3$, $R_4$, $R_5$, and $R_6$ are hydrogen.

The compound according to the present invention may be selected from compounds represented by Formulae 1a to 1d.

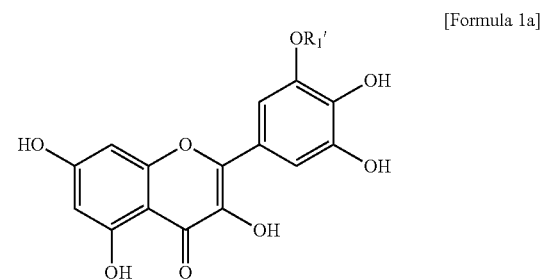

[Formula 1a]

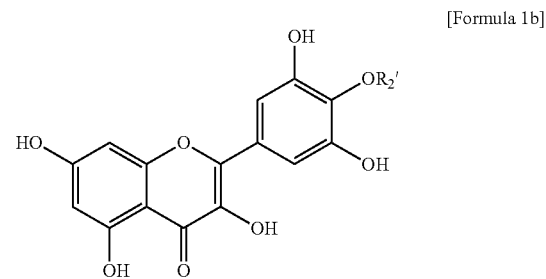

[Formula 1b]

-continued

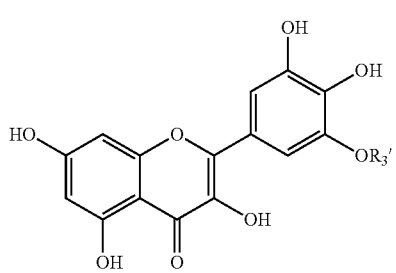

[Formula 1c]

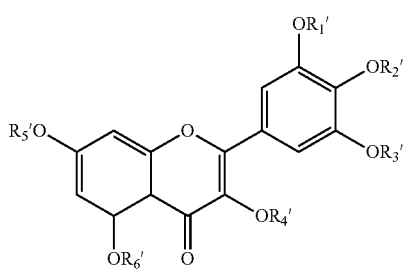

[Formula 1d]

wherein, in formulae 1a to 1d above,
each of $R_1'$, $R_2'$, $R_3'$, $R_4'$, $R_5'$, and $R_6'$ is independently linear or branched, saturated or unsaturated $C_{1-20}$ acyl, and
the acyls may be identical to or different from each other.

Another embodiment of the present invention also provides a method of preparing a compound represented by Formula 1 below, including acylating myricetin using an acyl donor in the presence of a lipase catalyst:

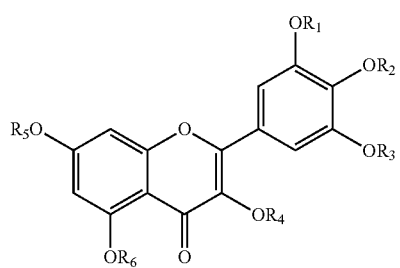

[Formula 1]

wherein, in Formula 1 above,
each of $R_1$, $R_2$, $R_3$, $R_4$, $R_5$, and $R_6$ is independently hydrogen, or linear or branched, saturated or unsaturated $C_{1-20}$ acyl,
the acyls may be identical to or different from each other, and
not all of $R_1$, $R_2$, $R_3$, $R_4$, $R_5$, and $R_6$ are hydrogen.

In the present invention, the lipase catalyst may be derived from a bacterial strain belonging to *Alcaligenes* sp.

In the method, the acyl donor may be vinyl acetate, vinyl butyrate, vinyl octanoate, vinyl laurate, vinyl palmitate, vinyl stearate, or vinyl eicosanoate, but the present invention is not limited thereto.

In the method, the acyl donor may be used in an amount of 0.5 equivalent to 5 equivalents with respect to a reaction substrate.

In the method, acylation may be performed at a temperature of 40° C. to 65° C. for 20 hours to 60 hours by using water as a culture medium.

Another embodiment of the present invention also provides a method of preparing a compound represented by Formula 1 below, including acylating myricetin by reacting the same with a fatty acid as an acyl donor and oxalyl chloride in the presence of a base:

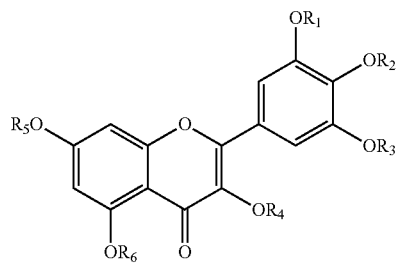

[Formula 1]

wherein, in Formula 1 above,
each of $R_1$, $R_2$, $R_3$, $R_4$, $R_5$, and $R_6$ is independently hydrogen, or linear or branched, saturated or unsaturated $C_{1-20}$ acyl,
the acyls may be identical to or different from each other, and
not all of $R_1$, $R_2$, $R_3$, $R_4$, $R_5$, and $R_6$ are hydrogen.

In the present invention, the base may be, but is not limited to, pyridine.

In the method, the fatty acid as an acyl donor may be, but is not limited to, acetic acid, butyric acid, octanoic acid, lauric acid, palmitic acid, stearic acid, or archidic acid or eicosanoic acid.

In the method, the fatty acid as an acyl donor may be used in an amount of 5 equivalents to 50 equivalents with respect to a reaction substrate.

In the method, acylation may be performed at a temperature of 30° C. to 80° C. for 10 hours to 30 hours.

MODE OF THE INVENTION

Hereinafter, configurations and effects of the present invention will be described in further detail with reference to the following examples. However, these examples are provided for illustrative purposes only and are not intended to limit the scope of the present invention.

Example 1: Development of Screening System for Verifying Effect of SNARE Inhibitor Prodrug A system capable of conveniently identifying and rapidly screening the function of a prodrug having a function similar to that of a known botulinum neurotoxin (Botox) by using a fluorescence phenomenon was devised (see FIG. 1). A two-step experiment was carried out to examine characteristics of a prodrug functioning in vivo, but not in vitro. In the present example, CFP and YFP, which are fluorescent proteins, were subjected to binding to C-terminals of syntaxin 1A (STX1A) and VAMP2, which are neuronal SNARE proteins, respectively, thereby constructing a PC12 stable cell line expressing the two proteins (see FIG. 1B). Changes in a distance between the two fluorescent proteins were indirectly measured by observing a fluorescence resonance energy transfer (FRET) phenomenon between the fluorescent proteins. The cell line was transfected with a plasmid containing the neuropeptide Y (NPY)-RFP gene, and a total of three types of protein complexes (Syntaxin 1A-CFP, VAMP2-YFP, and NPY-RFP) was used in verifying in vivo effects of a prodrug (see FIG. 1A). In addition, in vitro effects of the prodrug were examined by observing a membrane fusion process through the FRET phenomenon by labeling an artificially produced lipid bilayer membrane with a fluorescent dye (NBD, Rhodamine B) (see FIG. 1C).

Figure 2:
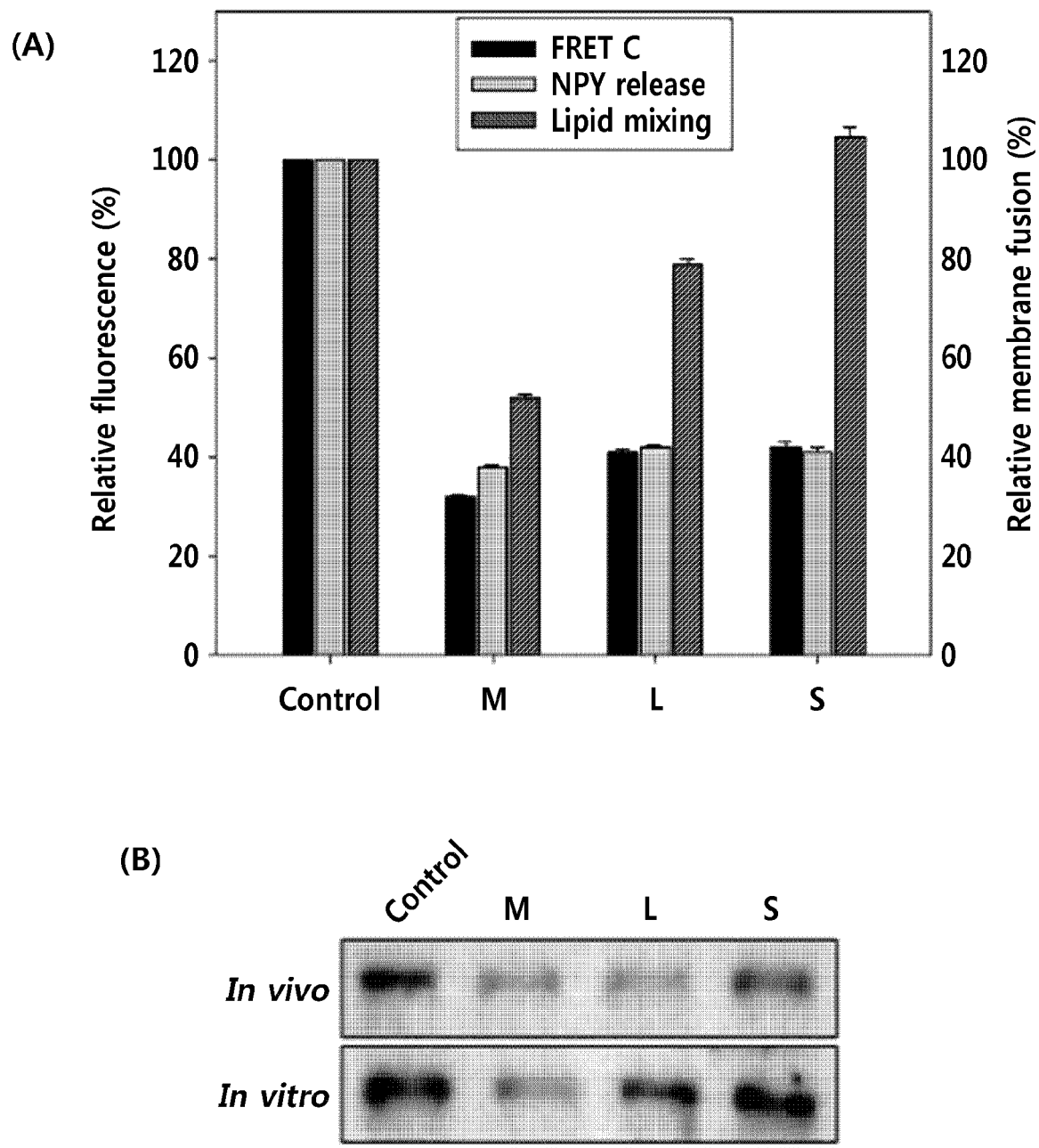
FIG. 2 illustrates verification results of SNARE-mediated membrane fusion inhibitory activities of laricitrin, combretol, and syringetin.

Example 2: Verification of SNARE-Mediated Membrane Fusion Inhibitory Activities of Laricitrin, Combretol, and Syringetin The functions of laricitrin, combretol, and syringetin were verified using the method of Example 1 (see FIG. 1) as a screening method capable of measuring the SNARE-mediated membrane fusion process (see FIG. 2). The binding of SNARE proteins was verified through a FRET change (FRET C) of the C-terminal of SNARE in PC12 cells, which are mammalian neurons, and, at the same time, content release was also verified by measuring the release of Y-RFP (NPY release), which is a neuropeptide. In addition, in verifying functions of candidate substances, in vivo functions were distinguished from in vitro functions by observing in vitro membrane fusion changes (see FIG. 2A). A control not treated with any substance (control), a myricetin-treated group (M) treated with myricetin known as a conventional SNARE complex formation inhibitor, a laricitrin-treated group (L), a combretol-treated group (C), and a syringetin-treated group (S) were compared with one another.

As a result, in the myricetin-treated group, both in vivo and in vitro functions decreased to 40% of those of the control or less, and this coincides with the results reported in previous studies. In contrast, laricitrin, combretol, and syringetin produced similar in vivo results (40% to 45% of the control) but significantly different in vitro results (85% to 90% of the control) compared to myricetin. These in vivo-specific characteristics suggest that laricitrin, combretol, and syringetin can be developed as prodrugs that effectively function only when absorbed in the body, and thus can effectively address disadvantages of conventional Botox or myricetin.

The above characteristics were clearly confirmed by immunoblotting of SNARE complexes (see FIG. 2B). SNARE complexes are known to have SDS-resistance, and based on these characteristics, immunoblotting using SDS-PAGE is generally used to identify the formation of SNARE complexes. Similarly to experimental results illustrated in FIG. 2A, myricetin showed a decreasing tendency in the formation of SNARE complexes both in vivo and in vitro, whereas laricitrin, combretol, and syringetin showed a decreasing tendency only in vivo (see FIG. 2B). Taken together, the above results indicate that laricitrin, combretol, and syringetin, which are myricetin derivatives, exhibit an in vivo-specific effect and thus can be developed as agents for prodrugs by using these characteristics.

Example 3: Preparation of Myricetin Derivatives by Acylation in Presence of Lipase Catalyst Myricetin has disadvantages in terms of chemical reactivity, skin permeability, and the like. In the present example, it was confirmed that these disadvantages could be addressed by reacting myricetin with an organic compound. The reaction is lipase-catalyzed acylation in which hydrogen bonded to a carbon atom of an aromatic hydrocarbon is substituted with an acyl group (RCO—). As in Reaction Scheme below, the aforementioned disadvantages may be addressed through the lipase-catalyzed acylation of myricetin.

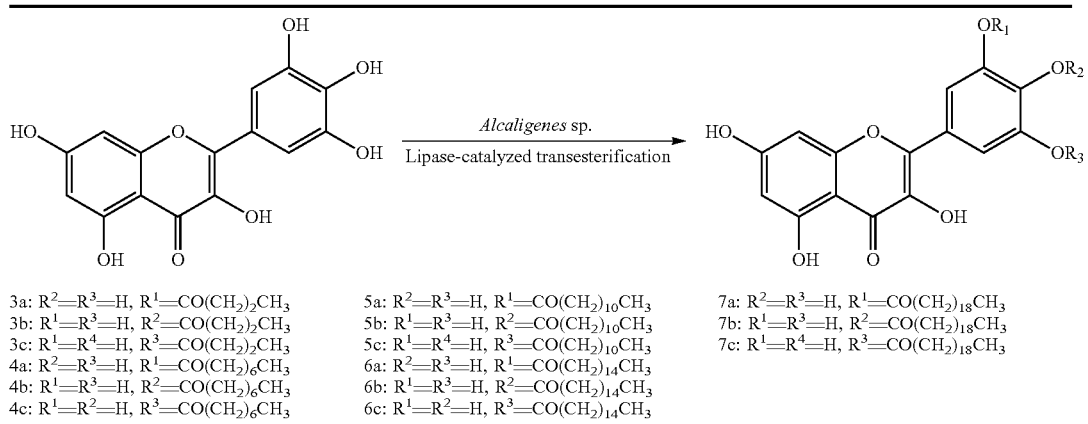

3a: $R^2=R^3=H$, $R^1=CO(CH_2)_2CH_3$
3b: $R^1=R^3=H$, $R^2=CO(CH_2)_2CH_3$
3c: $R^1=R^4=H$, $R^3=CO(CH_2)_2CH_3$
4a: $R^2=R^3=H$, $R^1=CO(CH_2)_6CH_3$
4b: $R^1=R^3=H$, $R^2=CO(CH_2)_6CH_3$
4c: $R^1=R^2=H$, $R^3=CO(CH_2)_6CH_3$

5a: $R^2=R^3=H$, $R^1=CO(CH_2)_{10}CH_3$
5b: $R^1=R^3=H$, $R^2=CO(CH_2)_{10}CH_3$
5c: $R^1=R^4=H$, $R^3=CO(CH_2)_{10}CH_3$
6a: $R^2=R^3=H$, $R^1=CO(CH_2)_{14}CH_3$
6b: $R^1=R^3=H$, $R^2=CO(CH_2)_{14}CH_3$
6c: $R^1=R^2=H$, $R^3=CO(CH_2)_{14}CH_3$

7a: $R^2=R^3=H$, $R^1=CO(CH_2)_{18}CH_3$
7b: $R^1=R^3=H$, $R^2=CO(CH_2)_{18}CH_3$
7c: $R^1=R^4=H$, $R^3=CO(CH_2)_{18}CH_3$

As an ester compound used in the reaction of myricetin, i.e., an acyl donor substrate, vinyl butyrate, vinyl octanoate, vinyl laurate, vinyl palmitate, or vinyl eicosanoate was used. The ester compounds used as substrates were compounds having an alkyl chain with 4, 8, 12, 16, or 20 carbon atoms.

Specifically, first, 318.24 mg of myricetin, 1 equivalent of each of a plurality of types of acyl donor substrates, and bacteria belonging to *Algaligenes* sp. (available from Meito Sangyo Co., Ltd) were mixed with 50 ml of water as a culture medium. The resulting mixture was incubated at 56° C. for 40 hours to allow an enzymatic reaction.

Next, the reaction solution was developed in thin layer chromatography to identify a spot corresponding to the compound. Thereafter, column chromatography (Product Name: "M.S.GEL", AGC Si-Tech CO., INC.) was performed to remove an unreacted acyl donor.

Figure 3:
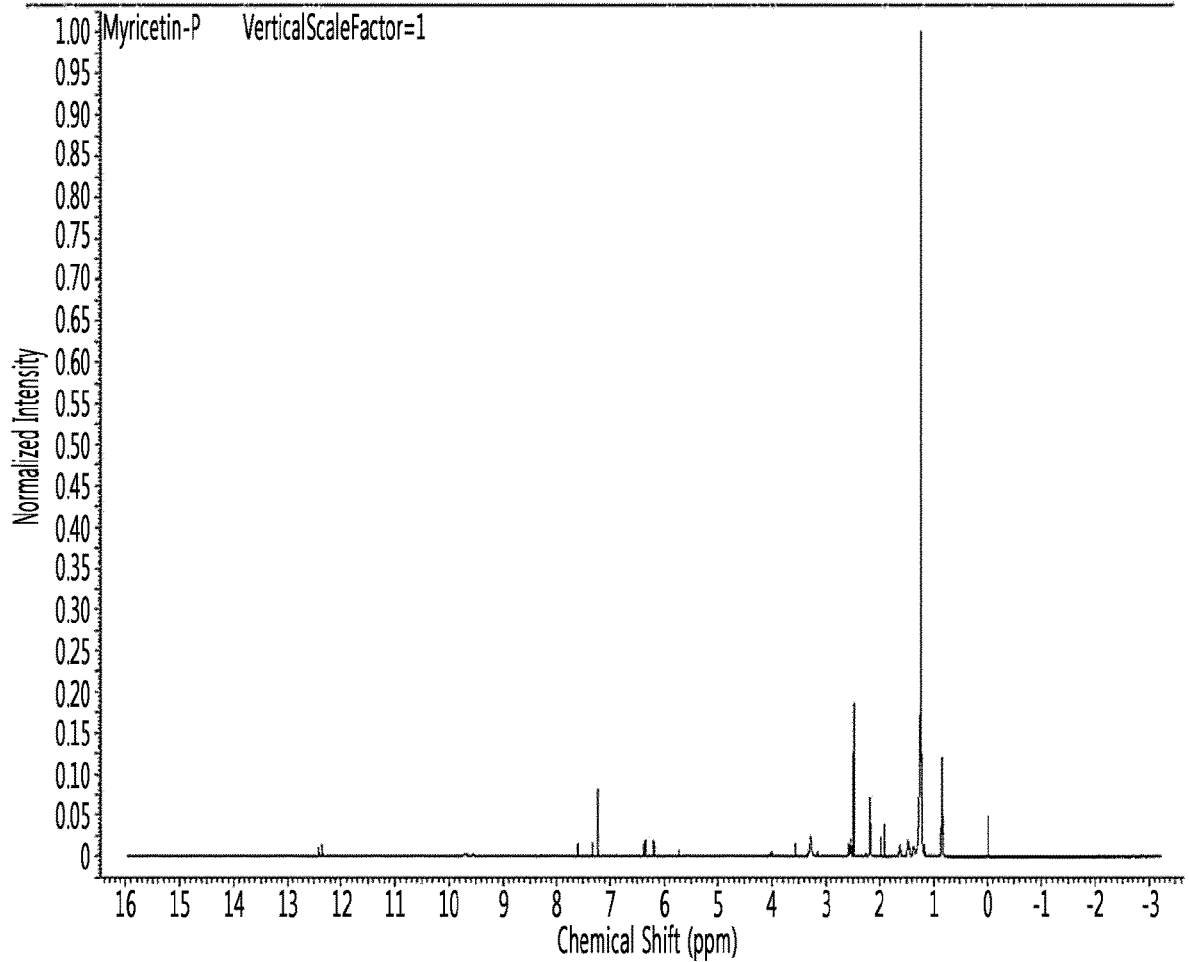
FIG. 3 illustrates $^1$H NMR analysis results of the structure and composition of a mixture of a partially acylated myricetin derivative produced by acylation using vinyl palmitate in the presence of a lipase catalyst, according to an embodiment of the present invention.

As a result of $^1$H NMR analysis of organic compounds, i.e., a series of myricetin derivatives, produced by acylation with the various acyl donors in the presence of a lipase catalyst (see FIG. 3), mixtures having compositions as shown in Table 1 below were obtained. C# in each compound name denotes the number of carbon atoms in the acyl group attached thereto.

TABLE 1

| Compounds | Regioisomer ratio | |
| --- | --- | --- |
| Myricetin-C4 | 3a:3b:3c | 32:47:21 |
| Myricetin-C8 | 4a:4b:4c | 35:40:25 |
| Myricetin-C12 | 5a:5b:5c | 29:35:36 |

TABLE 1-continued

| Compounds | Regioisomer ratio | |
|---|---|---|
| Myricetin-C16 | 6a:6b:6c | 39:37:24 |
| Myricetin-C20 | 7a:7b:7c | 38:36:26 |

Example 4: Preparation of Myricetin Derivatives by Acylation Using Base and Oxalyl Chloride As in Reaction Scheme below, myricetin derivatives were prepared by subjecting myricetin to acylation using a fatty acid by using a base and oxalyl chloride.

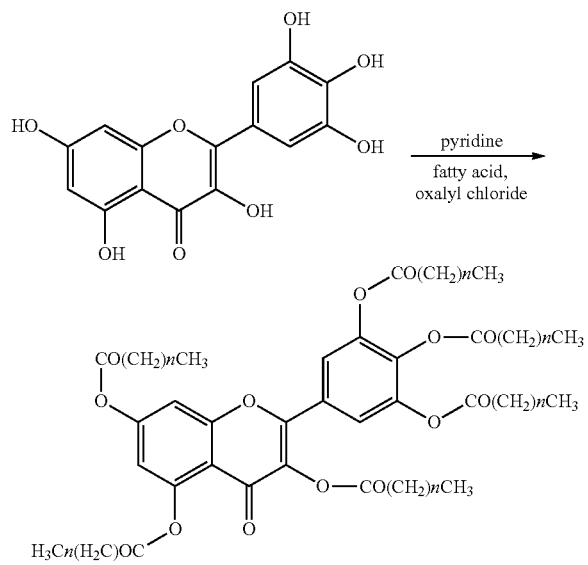

As the fatty acid used as an acyl donor, acetic acid, butyric acid, octanoic acid, lauric acid, palmitic acid, stearic acid, or archidic acid or eicosanoic acid was used. The fatty acids used as acyl donors were fatty acids having an alkyl chain with 2, 4, 8, 12, 16, 18, or 20 carbon atoms.

In particular, each of a plurality of types of acyl donors (2844.8 mg of stearic acid, 2564.2 mg of palmitic acid, and 2003.1 mg of lauric acid) was first allowed to react with oxalyl chloride to prepare a highly reactive fatty acid. Subsequently, 318.24 mg of myricetin was mixed with a reaction product obtained from the reaction and 50 ml of pyridine base. The resulting mixed solution was slowly heated to a temperature equal to room temperature or higher (40° C.) to allow a reaction to occur and last for 16 hours.

Next, the reaction solution was developed in thin layer chromatography to identify a spot corresponding to the compound. Thereafter, column chromatography (Product Name: "M.S.GEL", AGC Si-Tech CO., INC.) was performed to remove unreacted myricetin. Thereafter, the corresponding compound was dissolved in water and then extracted with chloroform, and this process was repeated several times to obtain a compound with high purity.

Figure 5:
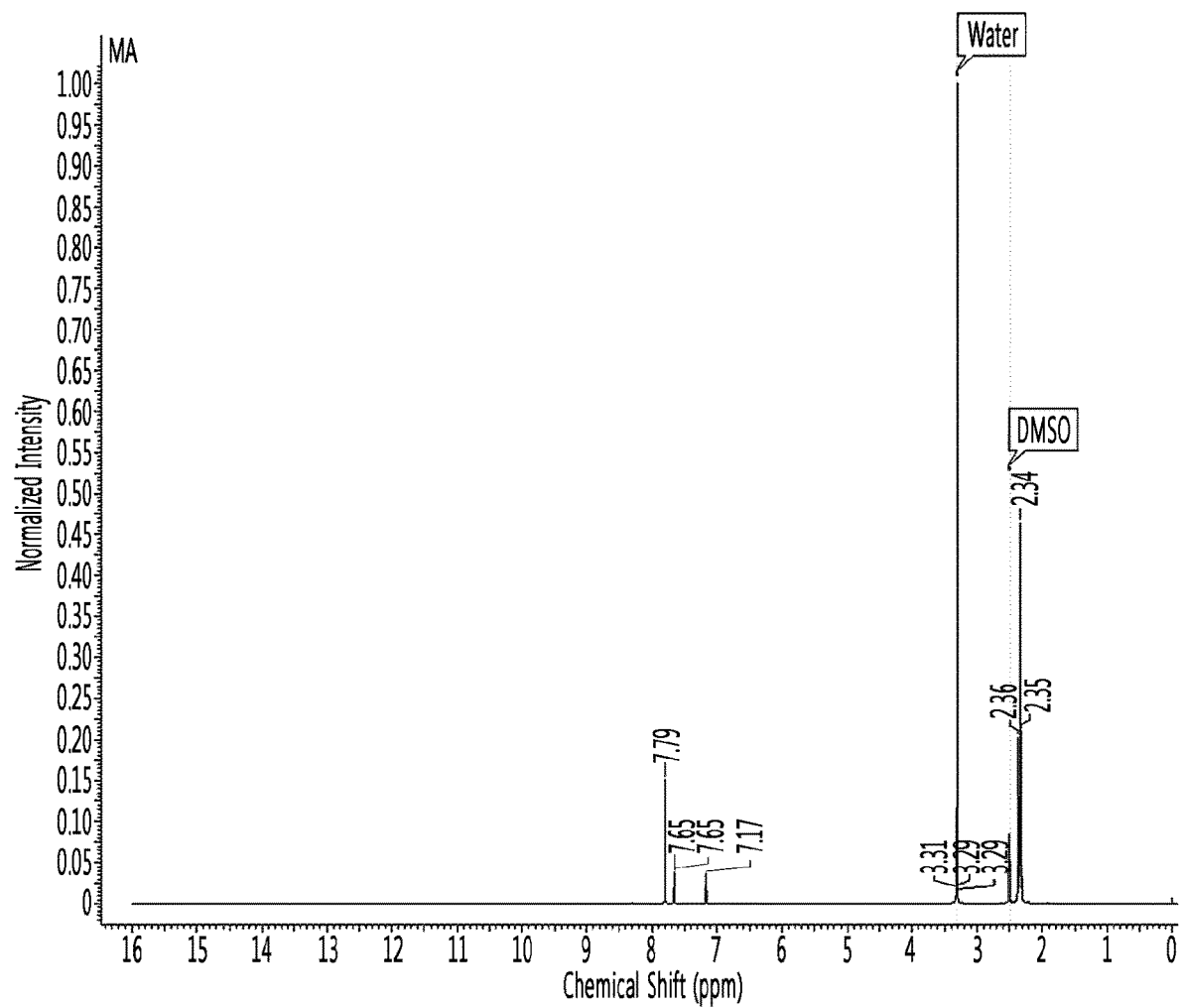
FIG. 5 illustrates $^1$H NMR analysis results of the structure and composition of a mixture containing a myricetin derivative, in which all hydroxyl groups of myricetin were acylated, produced by acylation using acetic acid as a fatty acid, according to an embodiment of the present invention.
Figure 6:
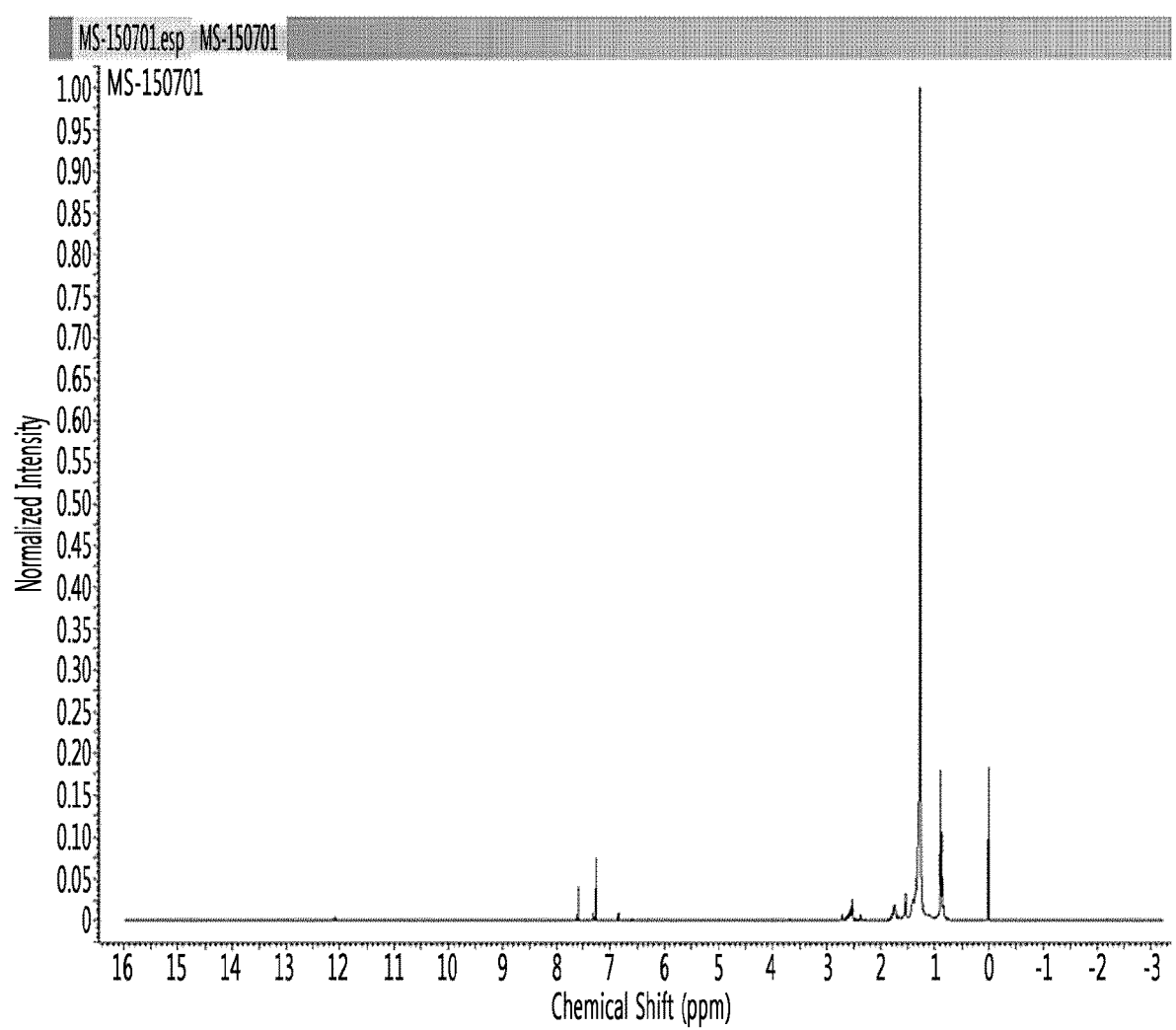
FIG. 6 illustrates $^1$H NMR analysis results of the structure and composition of a mixture containing a myricetin derivative, in which all hydroxyl groups of myricetin were acylated, produced by acylation using stearic acid as a fatty acid, according to another embodiment of the present invention.
Figure 7:
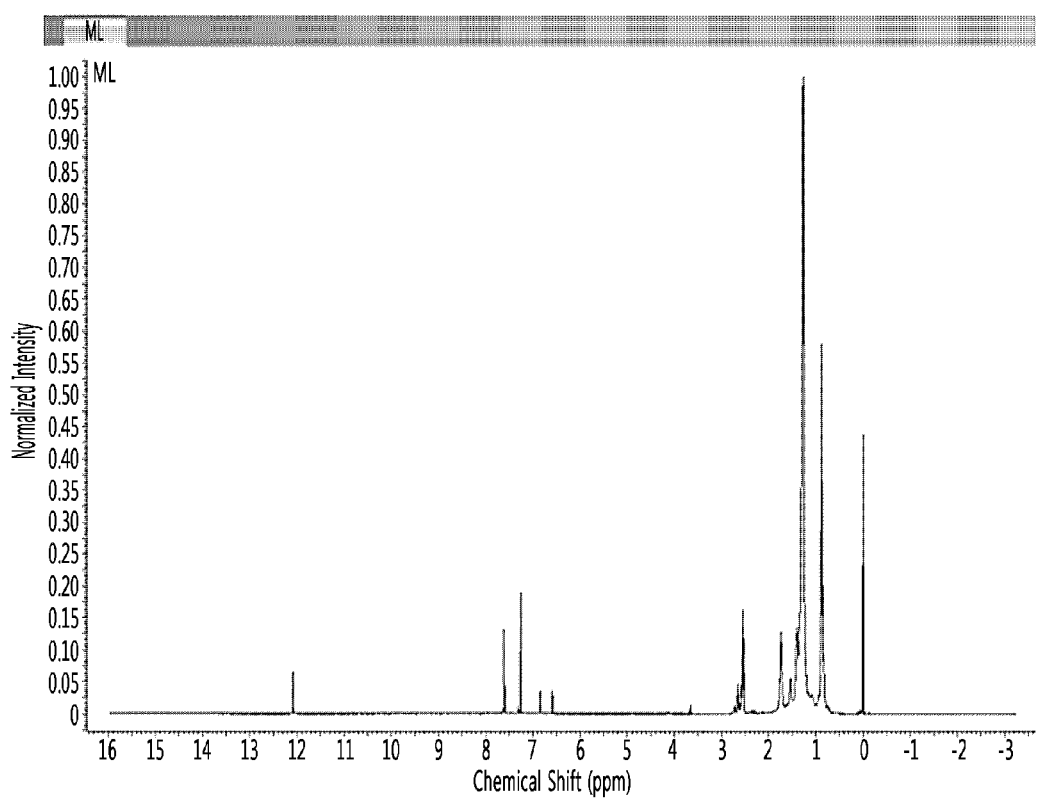
FIG. 7 illustrates $^1$H NMR analysis results of the structure and composition of a mixture containing a myricetin derivative, in which all hydroxyl groups of myricetin were acylated, produced by acylation using lauric acid as a fatty acid, according to still another embodiment of the present invention.

As described above, organic compounds, i.e., myricetin derivatives, prepared by acylation using a fatty acid and oxalyl chloride in the presence of a base catalyst were obtained. $^1$H NMR analysis results of a myricetin derivative obtained using palmitic acid as a fatty acid are illustrated in FIG. 4. In addition, $^1$H NMR analysis results of myricetin derivatives obtained using acetic acid, stearic acid, and lauric acid as fatty acids instead of palmitic acid are illustrated in FIGS. 5, 6, and 7, respectively.

Experimental Example 1: Experiment for Neurotransmitter Release Inhibition by Myricetin Derivatives The release rate of a neurotransmitter in response to the modified myricetin derivatives obtained in Example 3 was examined using the following two methods. Specific experimental methods are as described below.

The first method is as follows. In particular, PC12 cells were cultured to obtain 70% to 80% confluency in a culture dish. Subsequently, the PC12 cells were treated with a Krebs' buffer with high K$^+$ (56 mM NaCl, 1.2 mM MgSO$_4$, 2.5 mM CaCl$_2$, 68 mM KCl, 24 mM NaHCO$_3$, 2 mM KH$_2$PO$_4$, and 11 mM dextrose, pH 7.4), and incubated in a 5% CO$_2$ incubator at 37° C. for 5 minutes. Then, the PC12 cells were washed twice with a Krebs' buffer (118 mM NaCl, 1.2 mM MgSO$_4$, 2.5 mM CaCl$_2$, 5 mM KCl, 24 mM NaHCO$_3$, 2 mM KH$_2$PO$_4$, and 11 mM dextrose, pH 7.4) for 1 minute each, and then each of the myricetin derivatives (laricitrin: L, combretol: C, syringetin: S, 20 µM each) and [$^3$H] norepinephrine (1 ρCi/ml) were mixed into the culture medium, and then the medium was replaced. The PC12 cells were incubated in a 5% CO$_2$ incubator at 37° C. for 2 hours and then washed twice with a Krebs' buffer for 1 minute each. After thorough washing, the PC12 cells were washed four times with the culture medium for 15 minutes each. After the remaining medium was removed, the PC12 cells were washed twice with a Krebs' buffer for 1 minute each to collect basal level samples. The medium was replaced with Krebs' buffer with high K$^+$, followed by culturing for 10 minutes, to collect samples. The collected samples were subjected to radiation measurement using a liquid scintillation counter.

Figure 8:
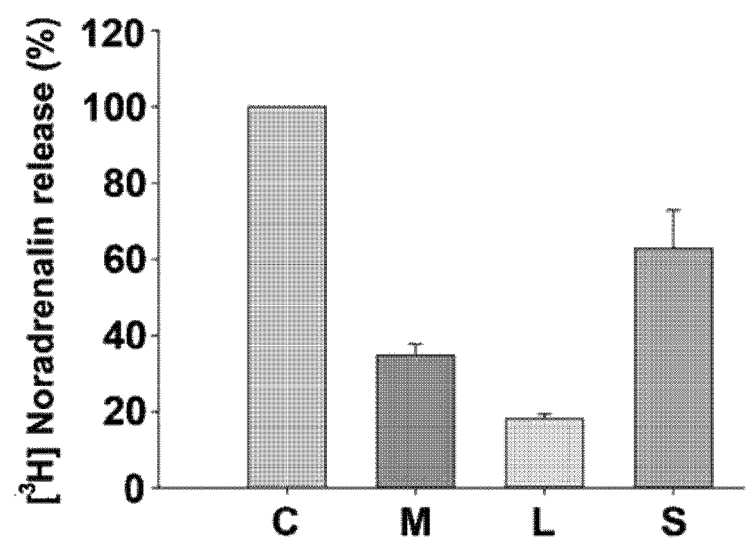
FIG. 8 illustrates examination results of the release rate of a neurotransmitter in response to syringetin and laricitrin.
Figure 9:
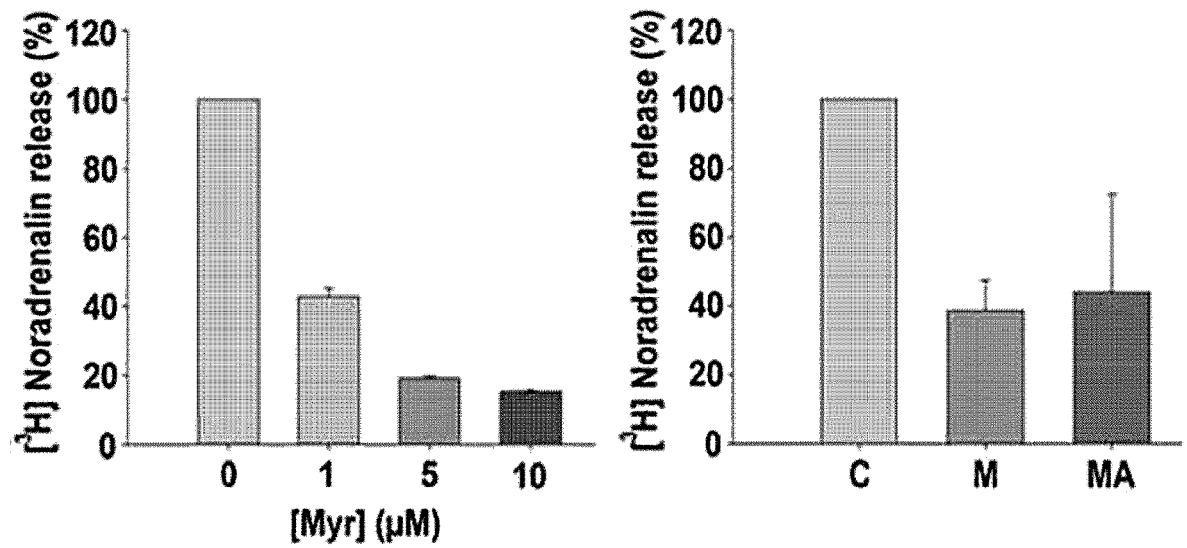
FIG. 9 illustrates examination results of the release rate of a neurotransmitter against a myricetin derivative obtained according to an embodiment of the present invention.

The results thereof are illustrated in FIGS. 8 and 9.

From the results in FIG. 8, it was confirmed that naturally occurring myricetin derivatives exhibited an effect of inhibiting the release of [$^3$H] norepinephrine, which is a neurotransmitter, and that laricitrin has the highest reactivity among these myricetin derivatives, exhibiting at least two-fold improved activity compared to conventional myricetin.

In addition, through the results in FIG. 9, it was confirmed that myricetin exhibited an effect of inhibiting the release of a neurotransmitter in a concentration-dependent manner, and a derivative (MA) obtained by reacting myricetin with acetic acid exhibited comparable or slightly better activity in comparison to myricetin.

The second method is as follows. In particular, PC12 cells were cultured to obtain 70% to 80% confluency in a culture dish. Subsequently, the PC12 cells were treated with a Krebs' buffer with high K$^+$ and incubated in a 5% CO$_2$ incubator at 37° C. for 15 minutes. The PC12 cells were washed twice with a Krebs' buffer for 1 minute each and each myricetin derivative was mixed in the culture medium, and then the medium was replaced. The PC12 cells were incubated in a 5% CO$_2$ incubator at 37° C. for 2 hours, and then washed with a Krebs' buffer for 1 minutes. After thorough washing, the PC12 cells were allowed to secrete a neurotransmitter into a Krebs' buffer with high K$^+$. The buffer containing the secreted neurotransmitter was quantified using a noradrenalin ELISA kit (IBL international), and results thereof are illustrated in FIG. 10.

Figure 10:
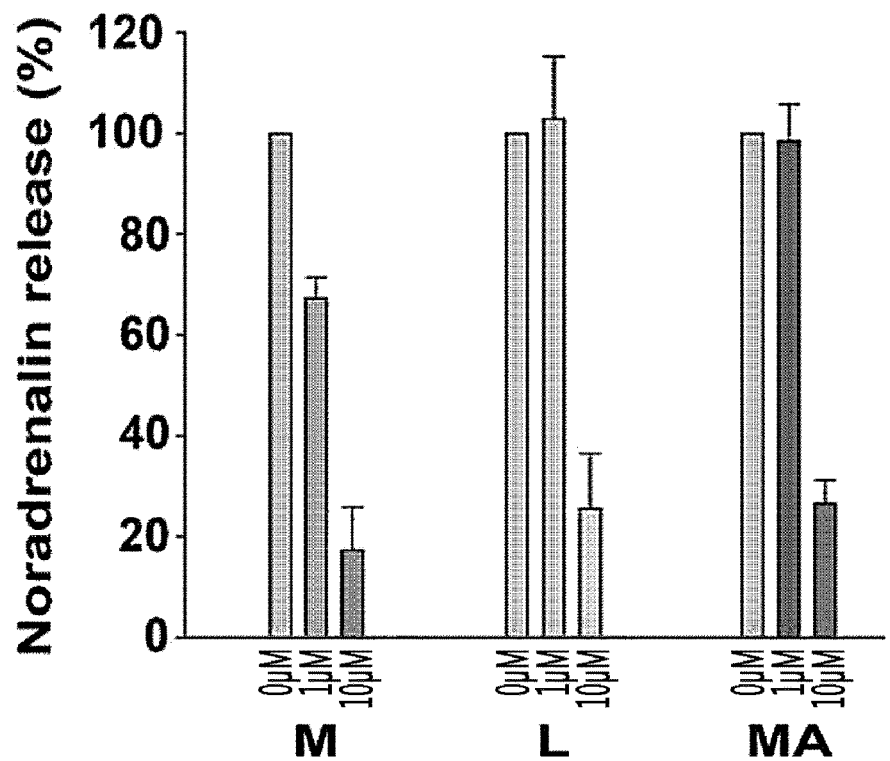
FIG. 10 illustrates examination results of the release rate of a neurotransmitter against a myricetin derivative obtained according to an embodiment of the present invention.

From the results in FIG. 10, it was confirmed that the myricetin derivative prepared by reacting laricitrin and acetic acid exhibited a neurotransmitter release inhibitory activity similar to that of conventional myricetin.

Experimental Example 2: Examination of Light Stability of Myricetin Derivatives The myricetin derivatives (laricitrin and syringetin) prepared using acetic acid as a fatty acid according to Example 4 were observed to show changes in various properties compared to myricetin, and whether the compound was denatured particularly when exposed to UV was examined.

First, 1 mg of each of myricetin and the myricetin derivatives were dissolved in 1 ml of dimethyl sulfoxide (DMSO), followed by mixing with zinc oxide having high reactivity with a hydroxyl group of myricetin. The resulting mixed solution was applied, as 100 µl drops, on 3M paper, and irradiated for 2 hours with UV light having an intensity of 253.7 nM using a UV lamp. As negative controls, untreated DMSO and a mixed solution of untreated DMSO and zinc oxide were used.

Figure 11:
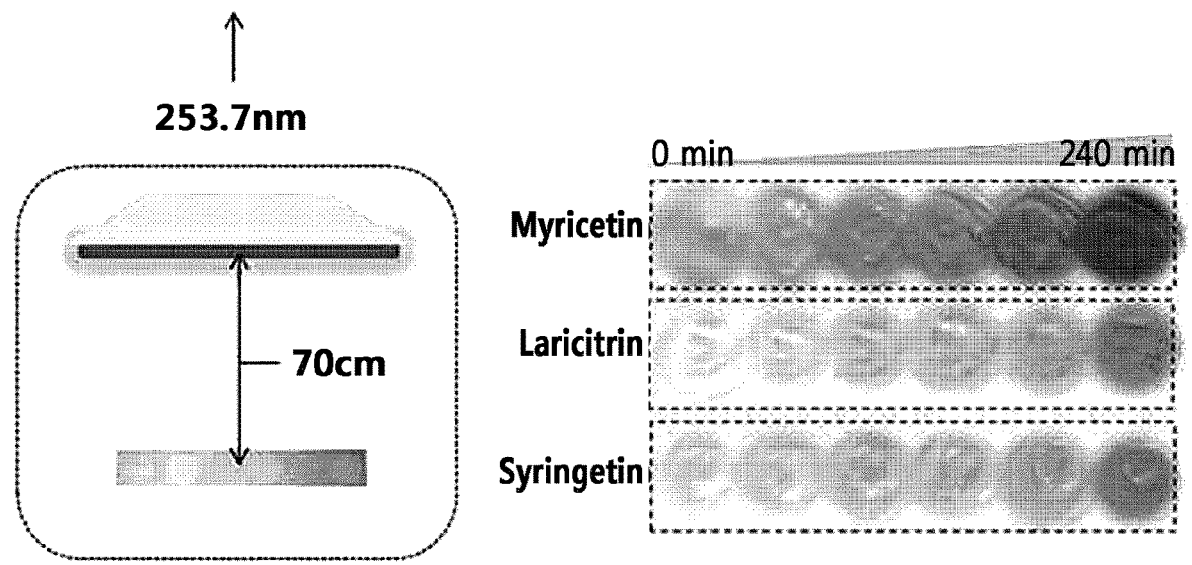
FIG. 11 illustrates examination results of the light stability of syringetin and laricitrin compared to myricetin.

The results thereof are illustrated in FIG. 11. Through the results in FIG. 11, it was confirmed that myricetin (M) showed color changes over time, whereas the myricetin derivatives showed no color change.

Experimental Example 3: Examination of Color Changes of Myricetin Derivatives In the present experimental example, whether a disadvantage of myricetin that a too dark intrinsic color thereof causes the skin to be stained can be addressed through making changes in properties using myricetin derivatives according to the present invention was examined.

Figure 12:
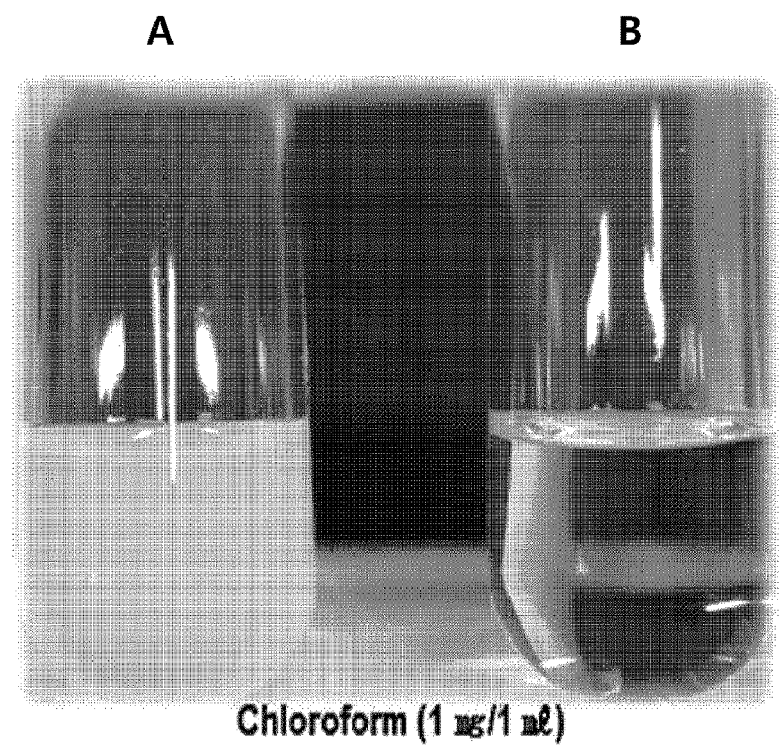
FIG. 12 illustrates solubility observation results of a case in which a myricetin derivative was dissolved in canola oil and mineral oil at a ratio of 1 mg/1 ml.

As a result, it was observed that as a degree to which a hydroxyl group of myricetin was acylated by palmitic acid, i.e., the degree of acylation, increased, colors of the myricetin derivatives were changed, unlike conventional myricetin. In particular, it was observed that the myricetin derivative obtained in Example 3, in which one hydroxyl group of myricetin was acylated by palmitic acid, had yellow color, which is an intrinsic color of myricetin (see FIG. 12A), whereas the myricetin derivative obtained in Example 4, in which all hydroxyl groups of myricetin were acylated by palmitic acid, had white color (see FIG. 12B).

Experimental Example 4: Examination of Changes in Liposoluble Properties of Myricetin Derivatives In the present experimental example, in view of the fact that in Example 4, myricetin underwent various changes in properties during synthesis of a myricetin derivative, in which all hydroxyl groups of myricetin were acylated by palmitic acid, the solubilities of the myricetin derivative in an organic solvent, or in a commercially available liposoluble cosmetic, food product, or the like were measured.

Figure 13:
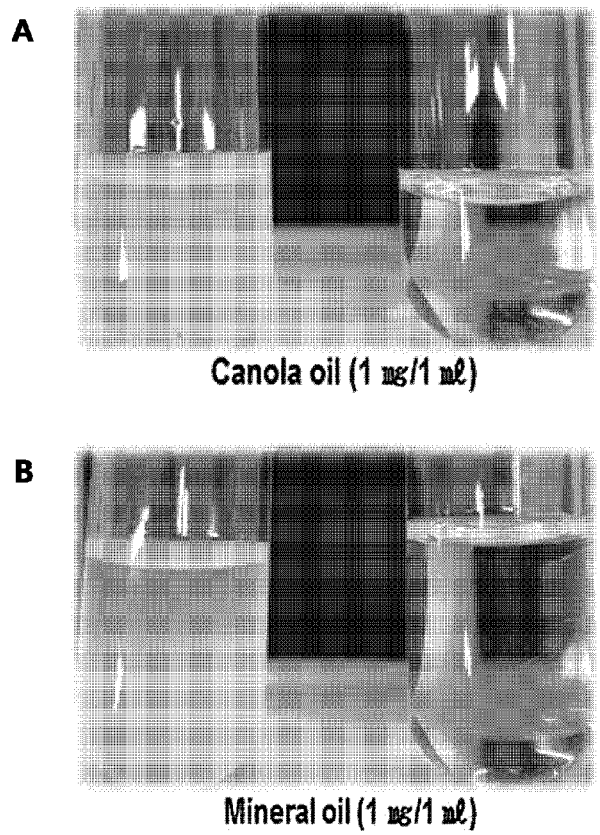
FIG. 13 is a set of images showing changes in the color of a myricetin derivative according to a degree to which a hydroxyl group of myricetin is acylated by palmitic acid, wherein A illustrates a case in which one hydroxyl group of myricetin is acylated by palmitic acid (Example 3), and B illustrates a case in which all hydroxyl groups of myricetin are acylated by palmitic acid (Example 4).

In particular, the myricetin derivative was dissolved in canola oil and mineral oil at a ratio of 1 mg/1 ml. The results thereof are illustrated in FIG. 13.

Conventional myricetin was seen to be insoluble in canola oil and mineral oil. However, as can be seen in FIG. 13, it was confirmed that the myricetin derivative according to the present invention, in which hydroxyl groups of myricetin were substituted by palmitic acid having a longer chain length, was liposoluble in canola oil (see FIG. 13A) and mineral oil (see FIG. 13B).

Such a liposoluble property enables the myricetin derivative to be easily dissolved in other cosmetic-based materials and is an important change for myricetin to be used as a cosmetic substance.

Experimental Example 5: Examination of Light Stability of Syringetin and Laricitrin It was examined whether myricetin, and laricitrin and syringetin, which are naturally occurring myricetin derivatives, were denatured when exposed to UV. First, each myricetin derivative (MP, 1 mg/1.34 g), prepared by reacting myricetin (M, 1 mg/1.34 g) and palmitic acid, was uniformly mixed in a commercially available sunblock cream (Kolmar Korea, NoTS UV protection sunscreen cream, 1.34 g), and the mixture was applied on a cover glass, followed by irradiation for 24 hours with UV having an intensity of 253.7 nM using a UV lamp.

Figure 14:
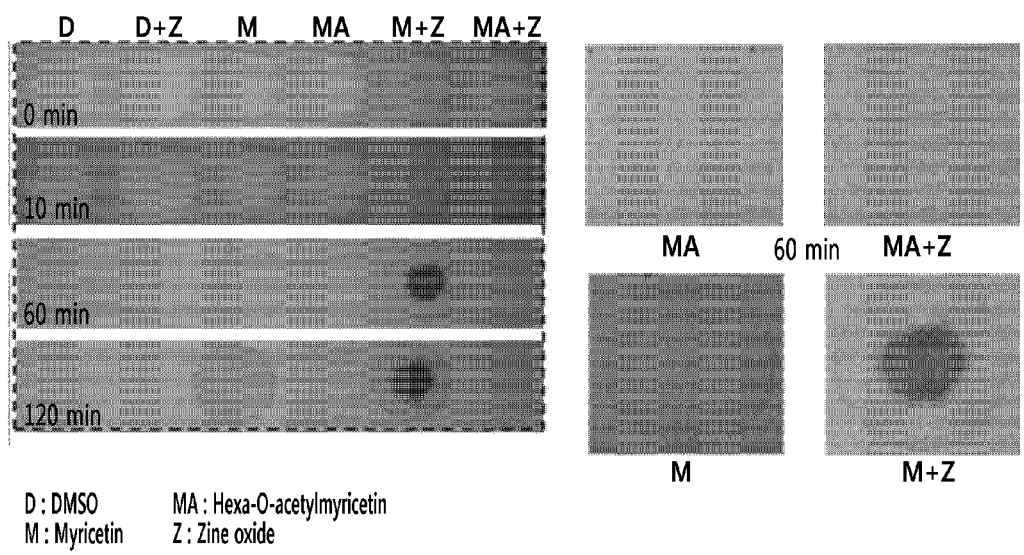
FIG. 14 illustrates examination results of the light stability of a myricetin derivative obtained according to an embodiment of the present invention.

After UV irradiation was completed, colors of samples were observed with the naked eye, and results thereof are illustrated in FIG. 14.

From the results in FIG. 14, it can be seen that the color of myricetin turned brown, indicating UV-caused denaturation, from an intrinsic yellow color at 5 minutes after UV irradiation, and turned dark brown at 30 minutes after UV irradiation, indicating complete oxidation. In contrast, syringetin and laricitrin did not show clear color changes compared to myricetin because denaturation by oxidation was reduced due to methoxylated hydroxyl groups. Laricitrin was deposited at 60 minutes after UV irradiation and turned brown, and syringetin was deposited at 240 minutes after UV irradiation and turned brown.

Experimental Example 6: Experiment for Bioconversion of Myricetin Derivative Obtained by Reaction with Acetic Acid A rate of bioconversion of the myricetin derivative prepared by acylation with acetic acid into myricetin in vivo was determined.

In particular, PC12 cells were cultured to obtain 70% to 80% confluency in a culture dish. Subsequently, the PC12 cells were treated with a Krebs' buffer with high $K^+$ and incubated in a 5% $CO_2$ incubator at 37° C. for 15 minutes. The PC12 cells were washed twice with a Krebs' buffer for 1 minute each and the myricetin derivative prepared by acylation with acetic acid was mixed into the culture medium, and then the medium was replaced. The PC12 cells were incubated in a 5% $CO_2$ incubator at 37° C. for 2 hours, and then washed with a Krebs' buffer for 1 minutes. After the cells were completely washed, the cells were treated with trypsin to collect trypsin-attached cells, and trypsin was removed therefrom to obtain only pure cells. The cells were suspended in 100 µl of tetrahydrofuran, followed by disruption through sonication, and then only tetrahydrofuran in which materials in the cells were lysed was collected. Subsequently, only myricetin in the recovered purified liquid was analyzed by high-performance liquid chromatography (HPLC) to examine whether the myricetin derivative prepared by acylation using acetic acid was converted into myricetin, and the results thereof are illustrated in FIG. 15.

Figure 15:
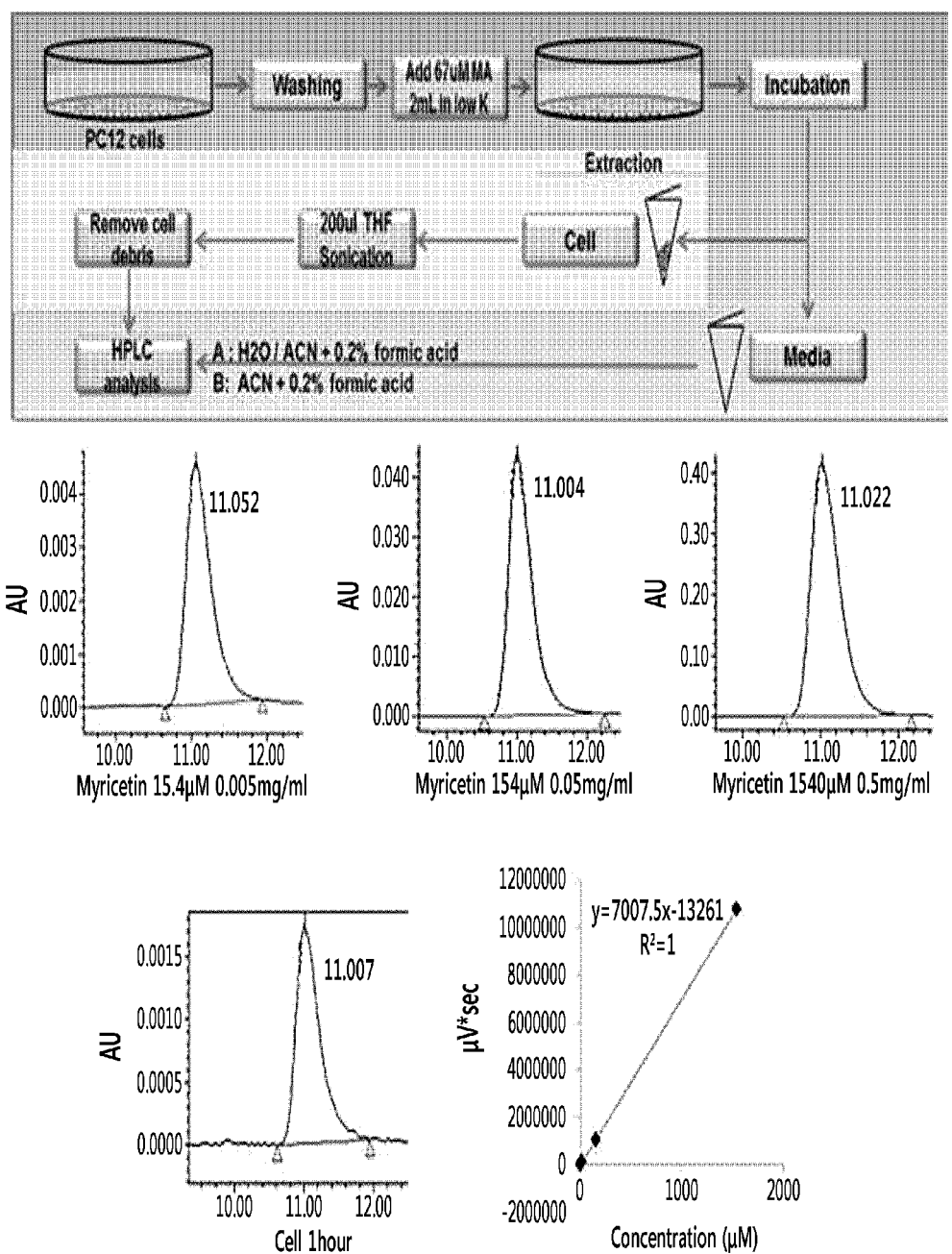
FIG. 15 illustrates examination results of an intracellular bio-conversion rate of a myricetin derivative obtained according to an embodiment of the present invention.

From the results in FIG. 15, it was confirmed that 3% of the myricetin derivative prepared by acylation using acetic acid was bioconverted into myricetin within 1 hour and had an activity.

Example 7: Hyperhidrosis Inhibitory Effect of Myricetin Derivative

It was examined whether the myricetin derivative according to the present invention actually exhibited an effect of inhibiting sweat secretion in the palm of a hand.

In particular, 1 mg of the myricetin derivative prepared by acylation using acetic acid according to Example 4 was mixed in 1 ml of the same commercially available sunblock cream as that used in Experimental Example 5. The resulting mixture of the sunblock cream and the myricetin derivative was applied on both hands of subjects under an ambient condition and in a hot room condition in which the subjects were producing a large amount of sweat from exercise. As the subjects, two men in their twenties who were considered to normally have hyperhidrosis were selected. For the first two days, the subjects were treated with only the sunblock cream not including the myricetin derivative, and for the following two days, the subjects were treated with the sunblock cream containing the myricetin derivative. The subjects were asked to hold weighed cosmetic cotton pads in their hands for 5 minutes, the cosmetic cotton pads were recovered and weighed again, and increased weights thereof were calculated.

Figure 16:
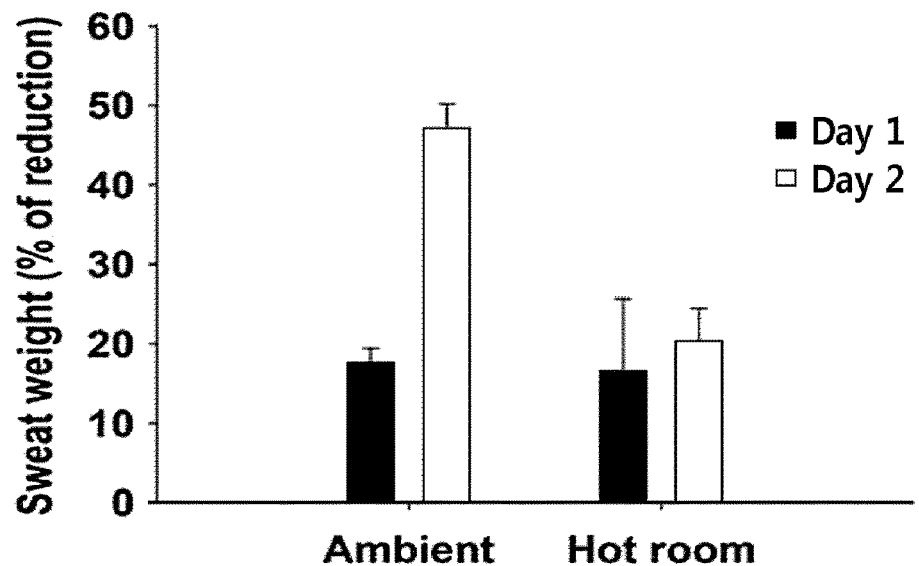
FIG. 16 illustrates results of examining whether a myricetin derivative obtained according to an embodiment of the present invention actually had an activity of inhibiting hyperhidrosis in vivo.
Figure 17:
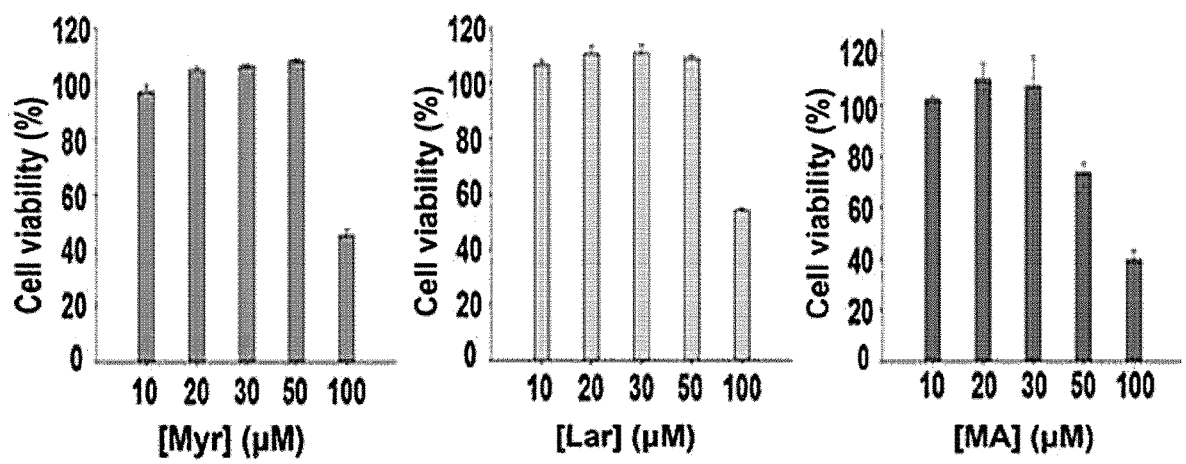
FIG. 17 illustrates examination results of the cell viability of myricetin, laricitrin, and a myricetin derivative obtained according to an embodiment of the present invention.

The results thereof are illustrated in FIG. 16.

From the results in FIG. 16, it was confirmed that the amount of sweat secreted from the hands of the subjects to which the myricetin derivative-containing sunblock cream had been applied was decreased by about 48% under the ambient condition. The amount of secreted sweat when the sweat had been induced by exercise was also reduced, but the degree of reduction decreased to about 20%.

The invention claimed is:

1. A method for inhibiting the formation of a soluble N-ethylmaleimide-sensitive factor attachment protein receptor (SNARE) complex comprising:
   administering one or more compounds selected from compounds represented by Formulae 1a, 1c, and 1e to 1g or a pharmaceutically acceptable salt thereof to a subject suffering from a symptom selected from a group consisting of hyperhidrosis, pore enlargement, and an allergy:

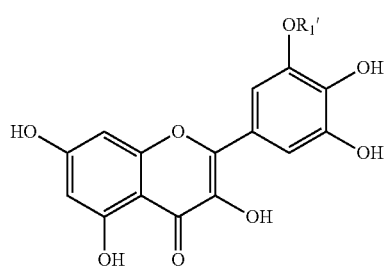

[Formula 1a]

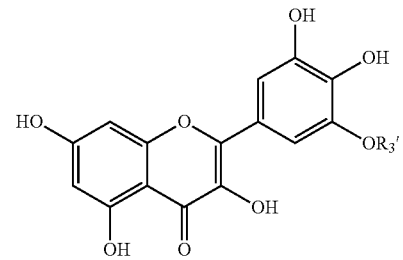

[Formula 1c]

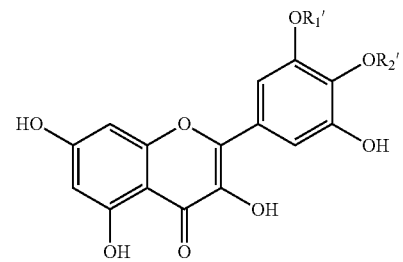

[Formula 1e]

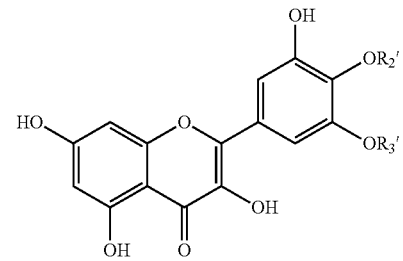

[Formula 1f]

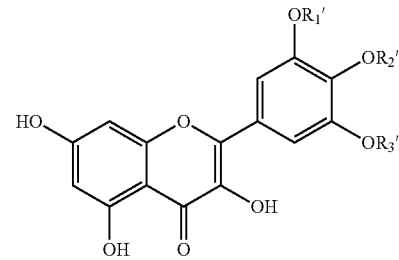

[Formula 1g]

wherein,
each of $R_1'$, $R_2'$, and $R_3'$ is independently linear or branched $C_1$-$C_4$ alkyl, or linear or branched, saturated or unsaturated $C_{1-20}$ acyl; and
the alkyls or the acyls are identical to or different from each other.

2. The method of claim 1, wherein the acyl group is selected from the group consisting of an acetyl group, a butyryl group, an octanoyl group, a lauroyl group, a palmitoyl group, a stearoyl group, and an eicosanoyl group.

3. A method for inhibiting the formation of a soluble N-ethylmaleimide-sensitive factor attachment protein receptor (SNARE) complex comprising:

administering a compound represented by Formulae 1 b or a pharmaceutically acceptable salt thereof to a subject suffering from a symptom selected from a group consisting of hyperhidrosis, pore enlargement, and an allergy:

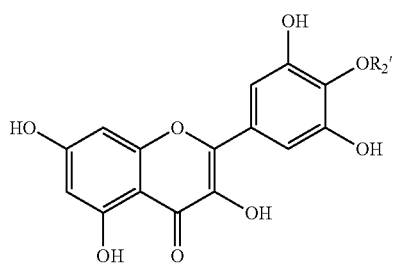

[Formula 1b]

wherein,
$R_2'$ is linear or branched $C_2$-$C_4$ alkyl, or linear or branched, saturated or unsaturated $C_{1-20}$ acyl.

4. A method for inhibiting the formation of a soluble N-ethylmaleimide-sensitive factor attachment protein receptor (SNARE) complex comprising:

administering a compound represented by Formulae 1b or a pharmaceutically acceptable salt thereof to a subject suffering from a symptom selected from a group consisting of hyperhidrosis and pore enlargement:

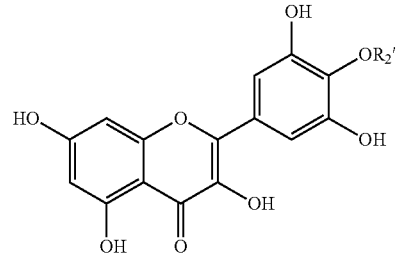

[Formula 1b]

wherein,
$R_2'$ is linear or branched $C_1$-$C_4$ alkyl, or linear or branched, saturated or unsaturated $C_{1-20}$ acyl.

* * * * *